(12) United States Patent
Hand et al.

(10) Patent No.: US 6,244,311 B1
(45) Date of Patent: **\*Jun. 12, 2001**

(54) METHOD AND APPARATUS FOR REMOVING AND DISPOSING OF BODY FLUIDS

(75) Inventors: Joseph M. Hand, Sheboygan Falls; Barry G. Anderson, Sheboygan; Michael C. Hollen, Manitowoc; Mark A. Miller, Kiel, all of WI (US)

(73) Assignee: Bemis Manufacturing Company, Sheboygan Falls, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/239,841

(22) Filed: Jan. 29, 1999

Related U.S. Application Data

(60) Continuation-in-part of application No. 08/877,771, filed on Jun. 17, 1997, now Pat. No. 5,871,476, which is a division of application No. 08/582,358, filed on Jan. 5, 1996, now Pat. No. 5,688,255, which is a continuation-in-part of application No. 08/547,759, filed on Oct. 24, 1995, now Pat. No. 5,683,371, which is a continuation-in-part of application No. 08/365,695, filed on Dec. 29, 1994, now Pat. No. 5,620,428.

(51) Int. Cl.[7] .............................. B65B 1/04; B65B 3/00; B67C 3/00

(52) U.S. Cl. ............................ 141/375; 141/4; 141/7; 141/8; 141/330; 141/360; 141/362; 141/364; 141/365; 141/366; 141/375; 604/317; 604/319; 604/322; 604/415

(58) Field of Search .......................... 604/317–322, 604/326, 415, 416; 128/DIG. 24; 141/4, 5, 7–9, 311 R, 319–321, 323, 330, 351, 360–366, 369, 370, 372, 375, 391

(56) References Cited

U.S. PATENT DOCUMENTS

| | | |
|---|---|---|
| 1,421,325 | 6/1922 | Walker et al. . |
| 1,693,885 | 12/1928 | Butterworth . |
| 1,827,085 | 10/1931 | Huff . |
| 2,004,027 | 6/1935 | Baxter ..................... 215/74 |
| 2,009,400 | 7/1935 | Hapgood ................ 226/116 |
| 2,073,746 | 3/1937 | Keller ....................... 15/14 |
| 2,208,028 | 7/1940 | Harrington ............. 226/125 |
| 2,438,769 | 3/1948 | Thomas . |
| 2,641,270 | 6/1953 | Allen . |
| 2,799,301 | 7/1957 | Ballard ................... 141/317 |
| 2,886,071 | 5/1959 | Rasmussen .............. 141/82 |
| 3,171,447 | 3/1965 | Fowler et al. ............ 141/95 |
| 3,363,627 | 1/1968 | Bidwell et al. ......... 128/276 |
| 3,394,831 | 7/1968 | Bathish et al. ........... 215/42 |
| 3,482,583 | 12/1969 | Fenn . |
| 3,603,328 | 9/1971 | Fenn . |
| 3,646,935 | 3/1972 | Holbrook et al. ...... 128/276 |
| 3,671,982 | 6/1972 | Sayles . |
| 3,699,964 | 10/1972 | Ericson .................. 128/275 |
| 3,768,478 | 10/1973 | Fertik et al. ............ 128/276 |
| 3,780,757 | 12/1973 | Jordan . |
| 3,782,414 | 1/1974 | Holbrook ................ 135/575 |
| 3,791,394 | 2/1974 | Hammelmann . |

(List continued on next page.)

FOREIGN PATENT DOCUMENTS

| | | |
|---|---|---|
| 0596132A1 | 5/1994 | (EP) . |
| 8602343 | 4/1986 | (WO) .................... B67C/1/04 |

OTHER PUBLICATIONS

Med Inc., Medical & Environmental Design, Inc.; Promotional Product Material, Jan. 15, 1991.

*Primary Examiner*—Timothy L. Maust
(74) *Attorney, Agent, or Firm*—Michael Best & Friedrich LLP

(57) ABSTRACT

A medical apparatus and method for draining bodily fluid from a container, such as a suction canister.

30 Claims, 20 Drawing Sheets

U.S. PATENT DOCUMENTS

| | | | |
|---|---|---|---|
| 3,863,664 | 2/1975 | Holbrook et al. | 137/205 |
| 3,866,608 | 2/1975 | Reynolds et al. | 128/276 |
| 3,897,599 | 8/1975 | Artzer . | |
| 3,916,924 | 11/1975 | McGowan | 134/95 |
| 3,945,392 | 3/1976 | Deaton et al. | 137/205 |
| 3,958,730 | 5/1976 | Caldwell . | |
| 3,989,046 | 11/1976 | Pannier, Jr. et al. | 128/276 |
| 3,995,333 | 12/1976 | Stephens . | |
| 4,004,590 | 1/1977 | Muriot | 128/276 |
| 4,015,603 | 4/1977 | Kurtz et al. | 128/276 |
| 4,049,555 | 9/1977 | Matherne | 210/409 |
| 4,053,284 | 10/1977 | Posch | 23/259 |
| 4,058,412 | 11/1977 | Knapp et al. . | |
| 4,084,723 | 4/1978 | Parker . | |
| 4,090,635 | 5/1978 | Nelson et al. . | |
| 4,108,336 | 8/1978 | Anderson, Jr. . | |
| 4,112,948 | 9/1978 | Kurtz et al. | 128/276 |
| 4,135,515 | 1/1979 | Muriot | 128/276 |
| 4,157,718 | 6/1979 | Baehr | 128/276 |
| 4,195,633 | 4/1980 | Nehring et al. | 128/276 |
| 4,195,672 | 4/1980 | Freeman . | |
| 4,228,798 | 10/1980 | Deaton | 128/276 |
| 4,238,892 | 12/1980 | Geiss | 34/85 |
| 4,245,637 | 1/1981 | Nichols | 128/276 |
| 4,258,824 | 3/1981 | Kurtz et al. | 181/233 |
| 4,275,732 | 6/1981 | Gereg | 128/276 |
| 4,306,557 | 12/1981 | North | 128/276 |
| 4,341,568 | 7/1982 | Christensen | 134/21 |
| 4,345,342 | 8/1982 | Saito | 4/301 |
| 4,356,084 | 10/1982 | Hatton et al. . | |
| 4,363,340 | 12/1982 | Naftulin | 141/51 |
| 4,384,580 | 5/1983 | Leviton | 604/119 |
| 4,388,922 | 6/1983 | Telang | 604/319 |
| 4,429,803 | 2/1984 | Butterfield | 215/366 |
| 4,430,084 | 2/1984 | Deaton . | |
| 4,430,085 | 2/1984 | Ahrens | 604/321 |
| 4,455,140 | 6/1984 | Joslin | 604/317 |
| 4,484,920 | 11/1984 | Kaufman et al. | 604/416 |
| 4,519,427 | 5/1985 | Ono et al. | 141/65 |
| 4,540,413 | 9/1985 | Russo | 604/320 |
| 4,559,664 | 12/1985 | Bohme et al. | 15/302 |
| 4,586,549 | 5/1986 | White | 141/67 |
| 4,629,159 | 12/1986 | Wellenstam | 251/149.6 |
| 4,631,050 | 12/1986 | Reed et al. | 604/4 |
| 4,666,063 | 5/1987 | Holoubek et al. | 222/107 |
| 4,673,006 | 6/1987 | Speck | 141/1 |
| 4,676,281 | 6/1987 | Nord | 141/1 |
| 4,676,287 | 6/1987 | Fitzwater | 141/285 |
| 4,685,480 | 8/1987 | Eck | 134/182 |
| 4,698,060 | 10/1987 | D'ntonio et al. | 604/320 |
| 4,704,106 | 11/1987 | Shave et al. | 604/319 |
| 4,715,855 | 12/1987 | D'Antonio et al. | 604/320 |
| 4,735,610 | 4/1988 | Akkas et al. | 604/119 |
| 4,740,202 | 4/1988 | Stacey et al. | 604/119 |
| 4,749,010 | 6/1988 | Petell | 141/59 |
| 4,762,241 | 8/1988 | Lang . | |
| 4,770,787 | 9/1988 | Heath et al. | 210/646 |
| 4,781,707 | 11/1988 | Boehringer et al. | 604/317 |
| 4,785,963 | 11/1988 | Magley | 220/266 |
| 4,795,428 | 1/1989 | Hwang | 604/73 |
| 4,795,448 | 1/1989 | Stacey et al. | 604/319 |
| 4,808,159 | 2/1989 | Wilson et al. | 604/4 |
| 4,809,860 | 3/1989 | Allen | 220/20.5 |
| 4,813,563 | 3/1989 | Ogden et al. . | |
| 4,820,351 | 4/1989 | Hambleton et al. | 134/21 |
| 4,857,063 | 8/1989 | Glenn | 604/317 |
| 4,863,446 | 9/1989 | Parker | 604/317 |
| 4,867,738 | 9/1989 | Mintz | 604/4 |
| 4,870,975 | 10/1989 | Cronk et al. | 128/749 |
| 4,889,531 | 12/1989 | D'Antonio et al. | 604/319 |
| 4,902,284 | 2/1990 | D'Antonio et al. | 604/320 |
| 4,905,325 | 3/1990 | Colditz . | |
| 4,913,179 | 4/1990 | Engel et al. | 134/113 |
| 4,913,197 | 4/1990 | Freidrich | 141/3 |
| 4,926,915 | 5/1990 | Deussen et al. | 141/290 |
| 4,955,874 | 9/1990 | Farrar et al. | 604/319 |
| 4,957,491 | 9/1990 | Parker . | |
| 4,961,440 | 10/1990 | Wright . | |
| 4,967,814 | 11/1990 | Day, Jr. | 141/286 |
| 4,969,491 | 11/1990 | Kiplinger | 141/1 |
| 4,972,976 | 11/1990 | Romero . | |
| 5,011,470 | 4/1991 | Kurtz et al. | 604/4 |
| 5,024,613 | 6/1991 | Vasconcellos et al. | 604/4 |
| 5,026,358 | 6/1991 | Everett, Jr. et al. | 604/320 |
| 5,027,872 | 7/1991 | Taylor et al. | 141/347 |
| 5,033,492 | 7/1991 | Mertens et al. | 134/166 R |
| 5,045,077 | 9/1991 | Blake, III | 604/321 |
| 5,049,273 | 9/1991 | Knox | 210/406 |
| 5,053,026 | 10/1991 | Andersen et al. | 604/319 |
| 5,064,101 | 11/1991 | Richter et al. . | |
| 5,067,950 | 11/1991 | Broadnax, Jr. | 604/317 |
| 5,071,035 | 12/1991 | Kiplinger | 222/83.5 |
| 5,078,677 | 1/1992 | Gentelia et al. | 604/4 |
| 5,119,830 | 6/1992 | Davis | 128/771 |
| 5,121,778 | 6/1992 | Baker et al. | 141/319 |
| 5,154,712 | 10/1992 | Herweck et al. | 604/321 |
| 5,185,007 | 2/1993 | Middaugh et al. | 604/320 |
| 5,186,195 | 2/1993 | Wall . | |
| 5,192,439 | 3/1993 | Roth et al. | 210/485 |
| 5,195,994 | 3/1993 | Dieringer | 604/283 |
| 5,217,038 | 6/1993 | Pinder | 137/216 |
| 5,222,530 | 6/1993 | Baker et al. . | |
| 5,242,434 | 9/1993 | Terry | 604/317 |
| 5,273,083 | 12/1993 | Burrows | 141/18 |
| 5,300,050 | 4/1994 | Everett, Jr. et al. | 604/320 |
| 5,349,995 | 9/1994 | Perez | 141/98 |
| 5,351,859 | 10/1994 | Jansen | 222/82 |
| 5,380,314 | 1/1995 | Herweck et al. | 604/403 |
| 5,437,836 | 8/1995 | Yamada | 422/1 |
| 5,460,193 | 10/1995 | Levallois et al. . | |
| 5,470,324 | 11/1995 | Cook et al. | 604/319 |
| 5,546,979 | 8/1996 | Clark, II et al. | 137/318 |
| 5,599,331 | 2/1997 | Hemstreet et al. | 604/317 |
| 5,620,428 | 4/1997 | Hand | 604/317 |
| 5,624,417 | 4/1997 | Cook et al. | 604/319 |
| 5,637,103 | 6/1997 | Kerwin et al. | 604/317 |
| 5,683,371 | 11/1997 | Hand | 604/317 |
| 5,688,255 | 11/1997 | Hand | 604/317 |
| 5,725,516 | 3/1998 | Cook et al. | 604/319 |
| 5,741,237 | 4/1998 | Walker | 604/317 |
| 5,776,118 * | 7/1998 | Seifert et al. | 604/317 |
| 5,776,260 | 7/1998 | Dunn et al. | 134/18 |
| 5,807,359 | 9/1998 | Bemis et al. | 604/322 |
| 5,837,103 | 11/1998 | Trokhan et al. . | |
| 5,871,476 | 2/1999 | Hand | 604/317 |
| 5,901,717 | 5/1999 | Dunn et al. | 134/56 |
| 5,931,822 | 8/1999 | Bemis et al. | 604/322 |
| 6,027,490 * | 2/2000 | Radford et al. | 604/540 |

* cited by examiner

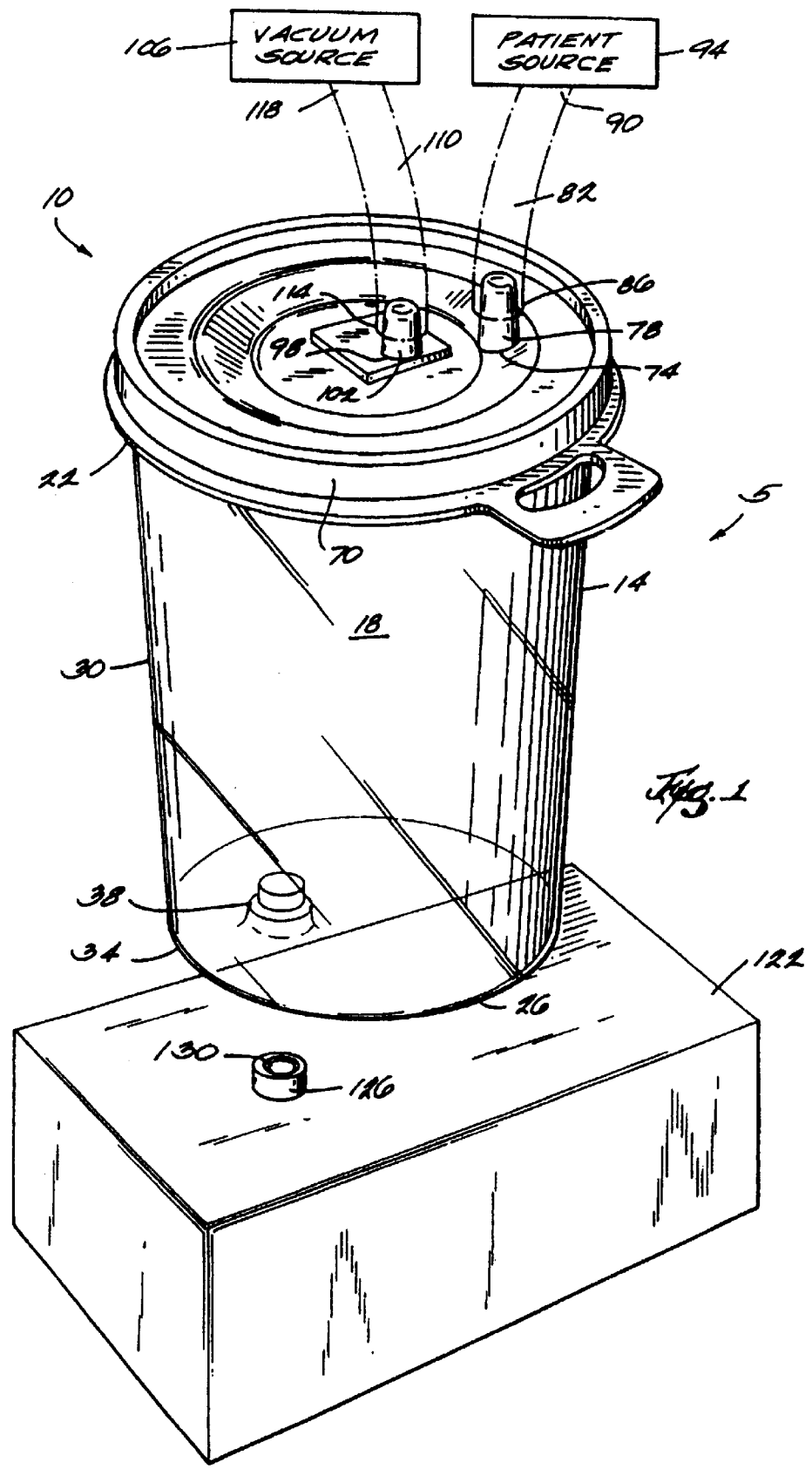

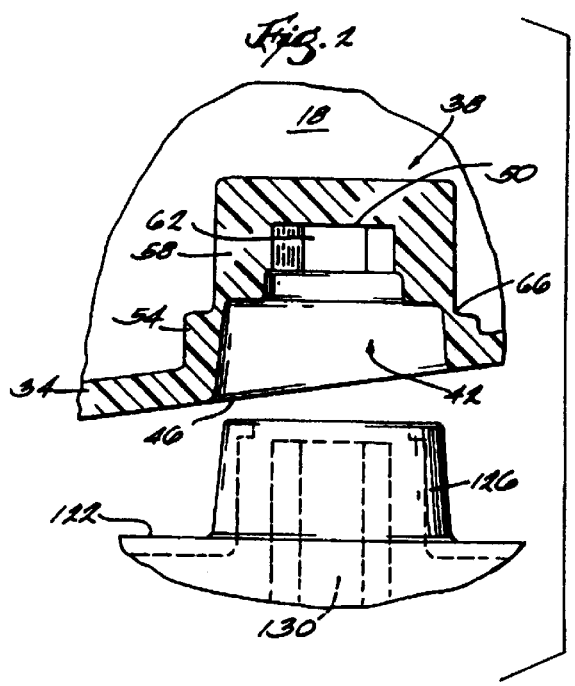
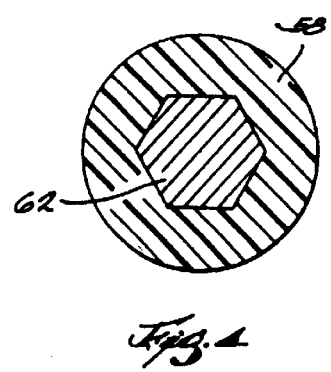
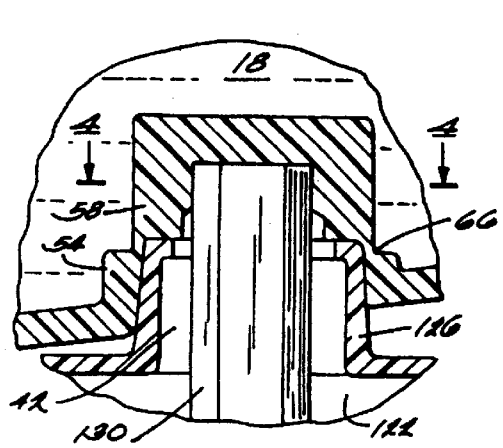
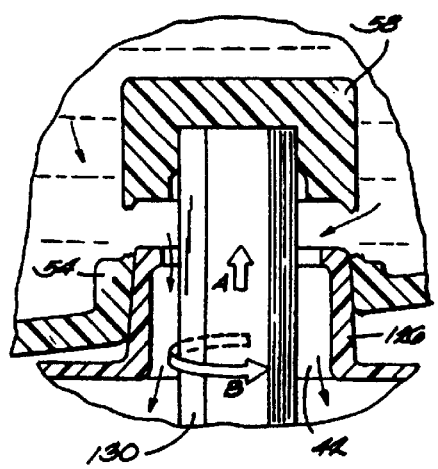

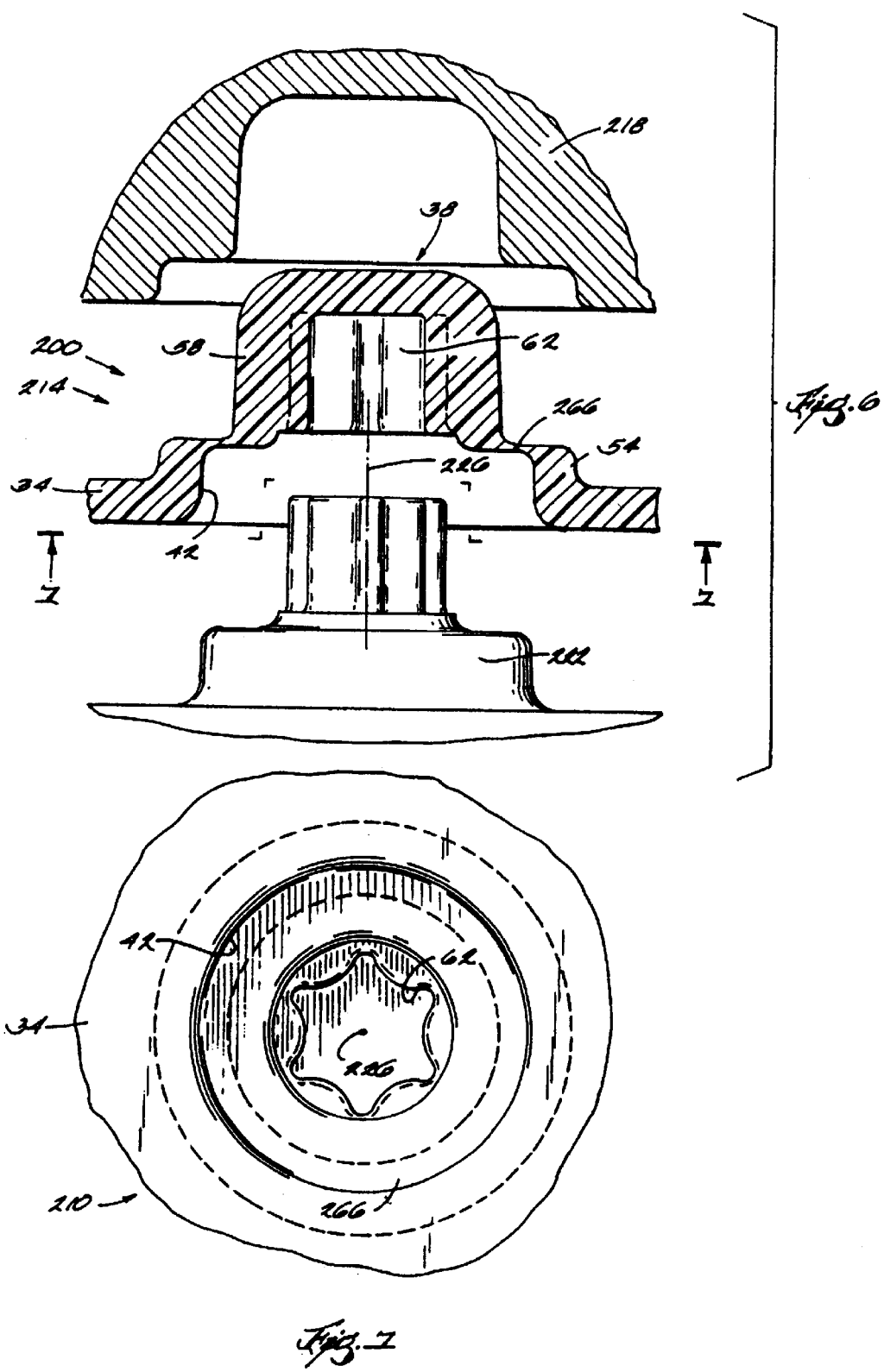

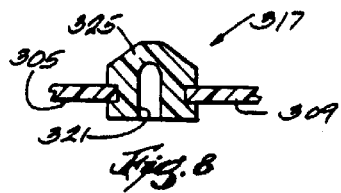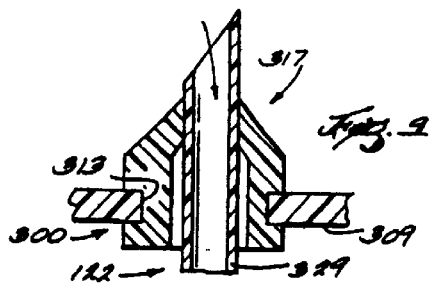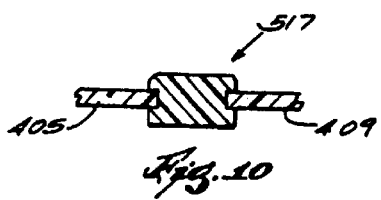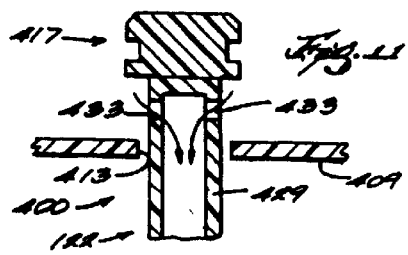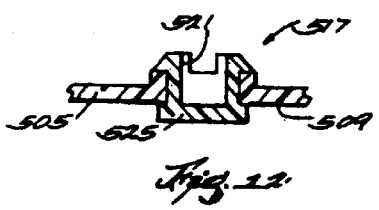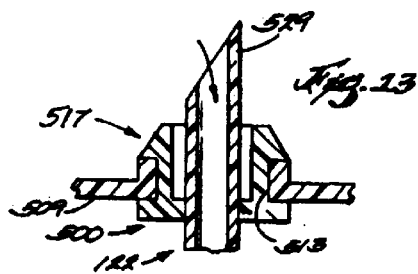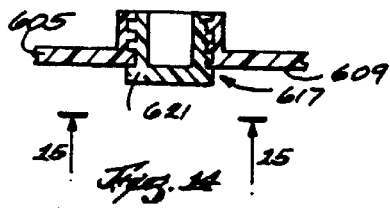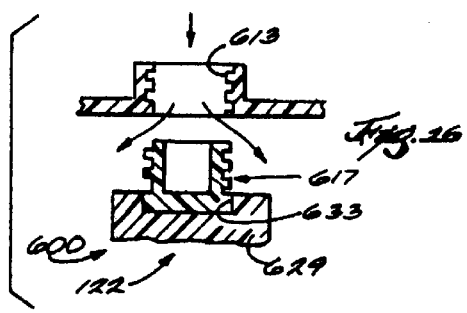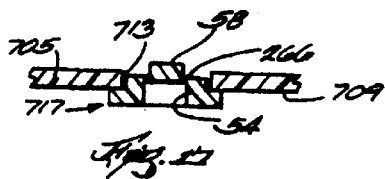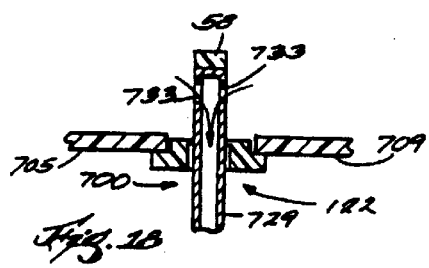

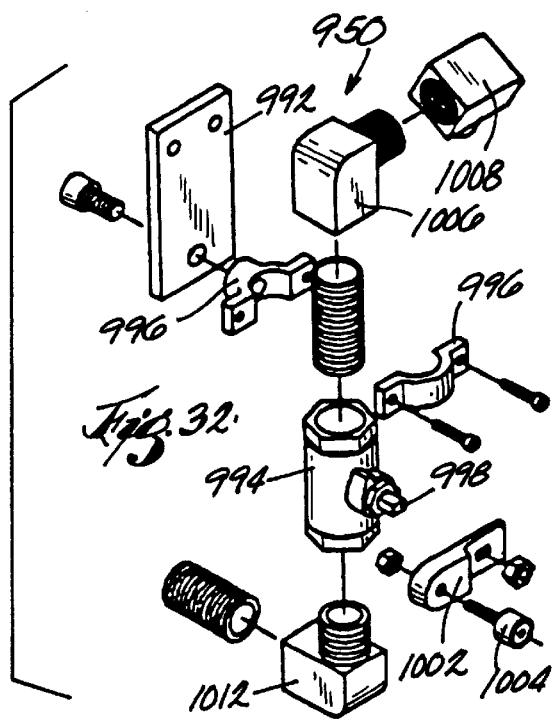
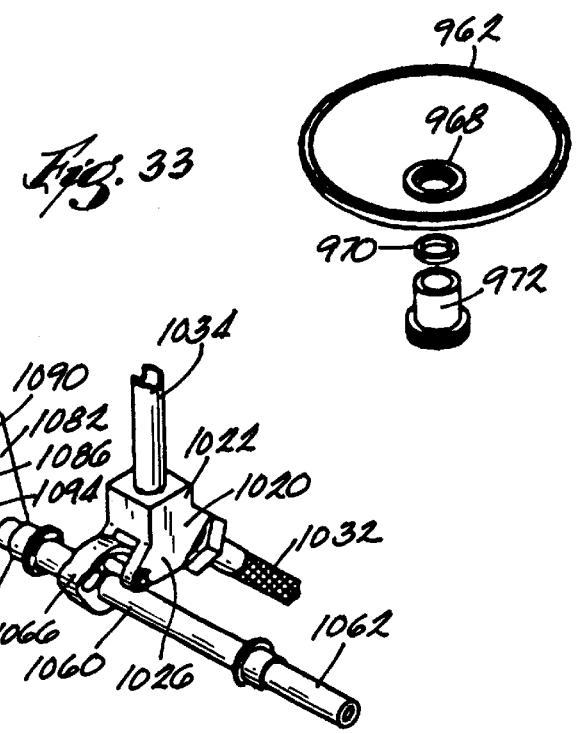

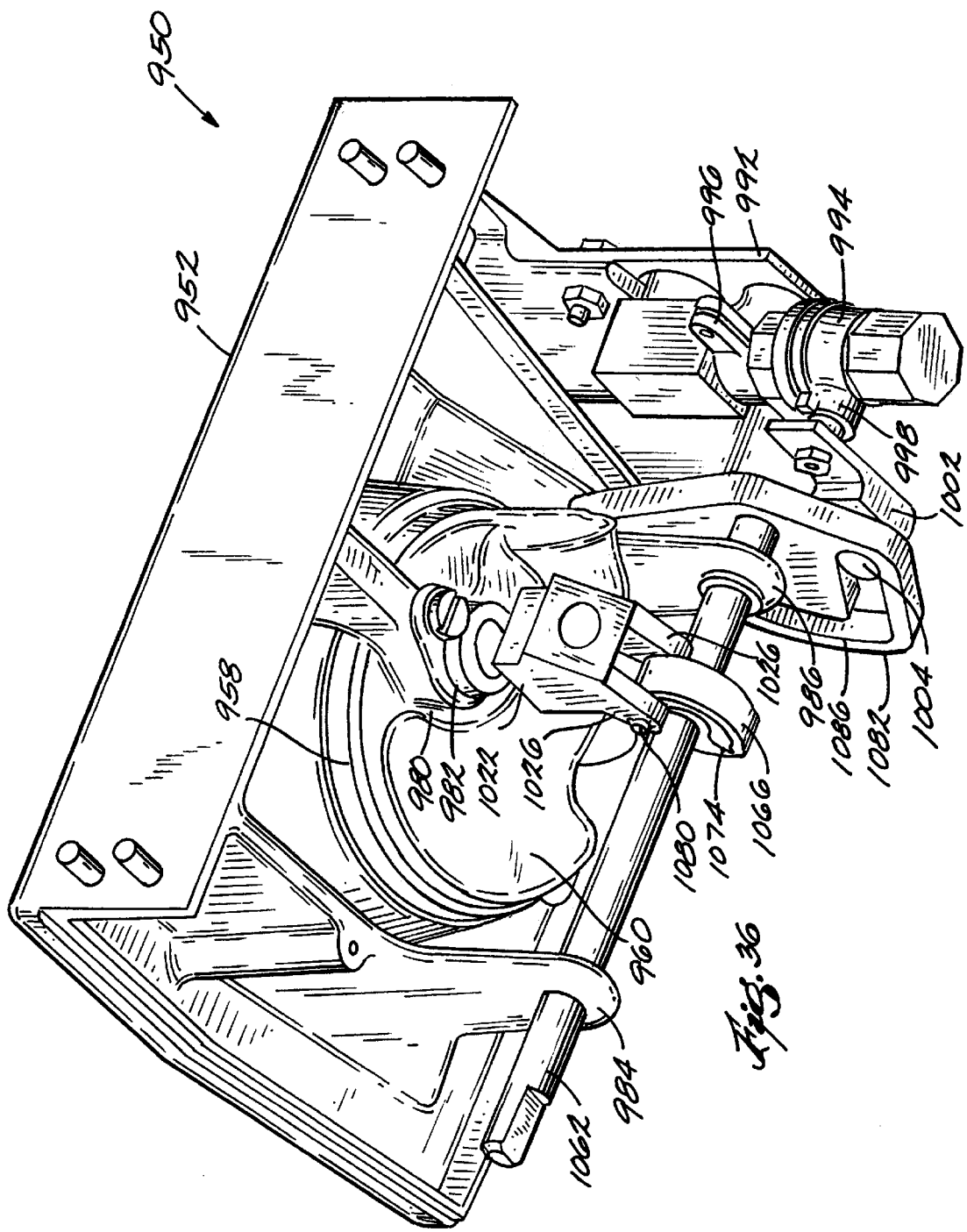

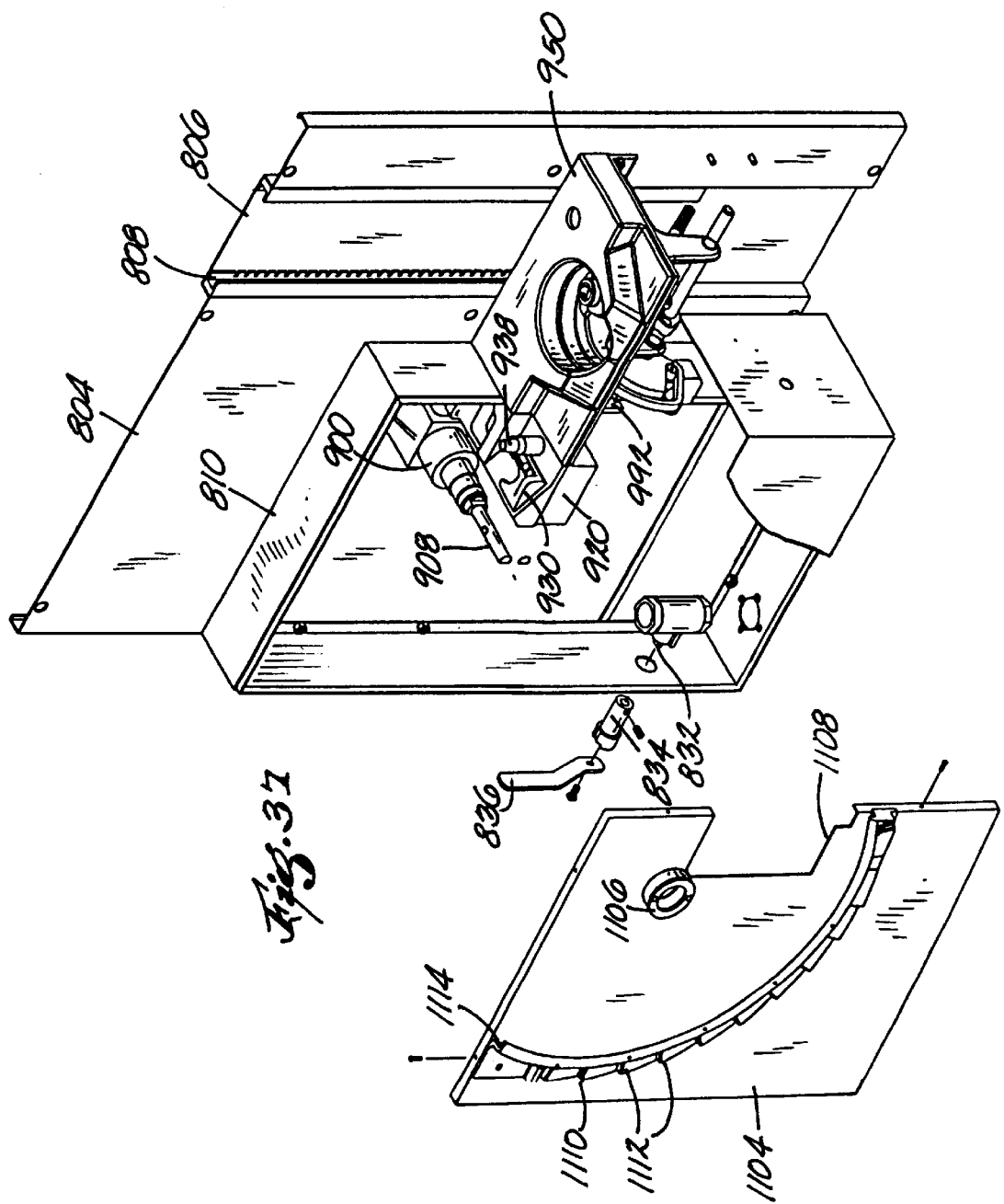

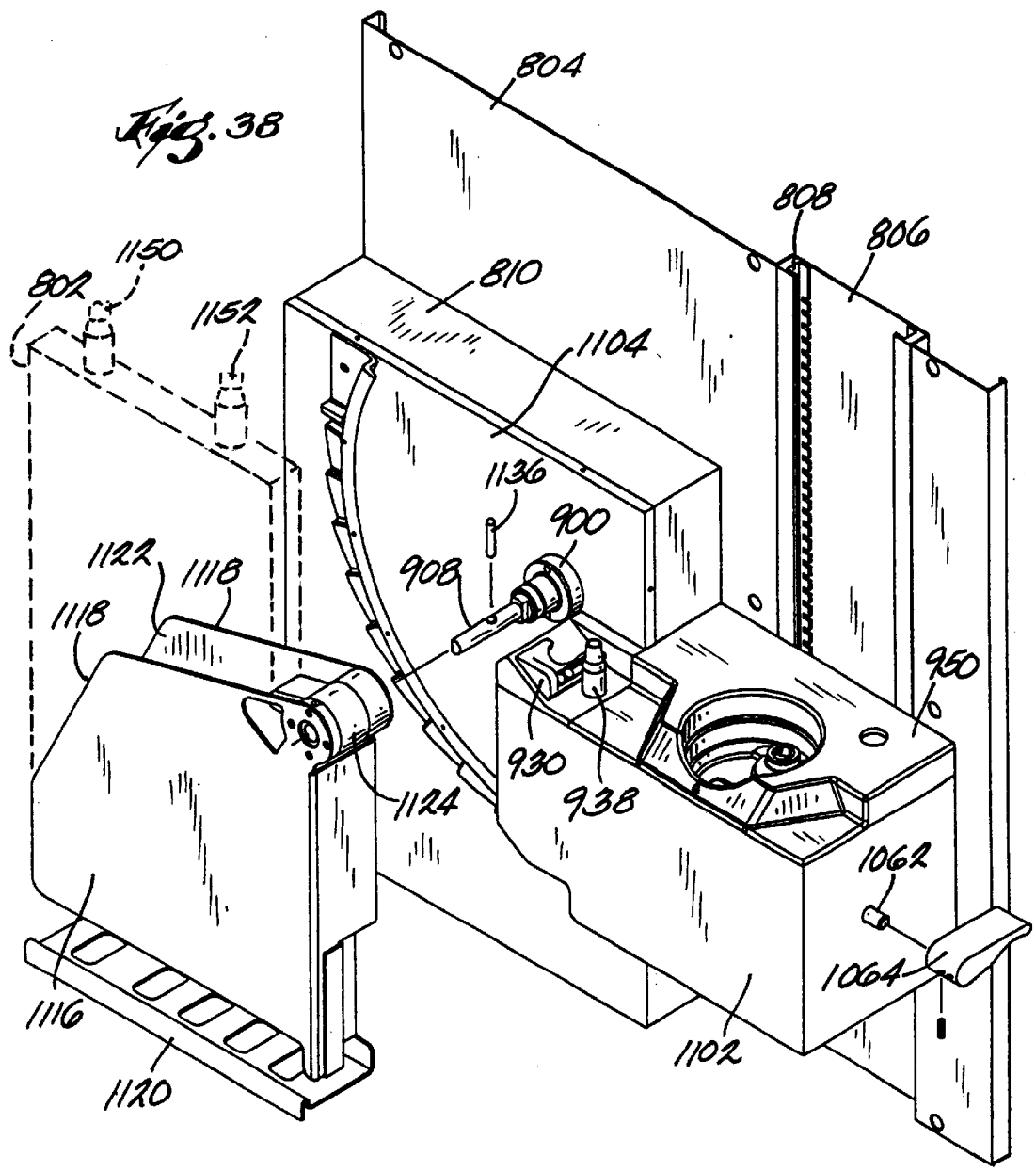

METHOD AND APPARATUS FOR REMOVING AND DISPOSING OF BODY FLUIDS

RELATED APPLICATIONS

This is a continuation-in-part of U.S. Ser. No. 08/877,771 filed Jun. 17, 1997, now U.S. Pat. No. 5,871,476, which is a divisional of U.S. Ser. No. 08/582,358 filed Jan. 5, 1996, now U.S. Pat. No. 5,688,255, which is a continuation-in-part of U.S. Ser. No. 08/547,759 filed Oct. 24, 1995, now U.S. Pat. No. 5,683,371, which is a continuation-in-part of U.S. Ser. No. 08/365,695 filed Dec. 29, 1994, now U.S. Pat. No. 5,620,428.

FIELD OF THE INVENTION

The invention relates to methods and apparatus for draining bodily fluid held in a container, such as a suction canister.

BACKGROUND OF THE INVENTION

Suction canisters are used in hospital environments and particularly during various surgical procedures to store drained bodily fluid from a patient. In general, suction canisters are used in conjunction with a vacuum source which enables bodily fluid to be drained from the patient and stored in the canister. Each canister generally includes a receptacle for holding the bodily fluid, a lid with a vacuum port and a patient port, a suction conduit connecting the vacuum port to a vacuum source, and a patient conduit for conveying the bodily fluid from the patient into the receptacle through the patient port. When the suction conduit is connected to the vacuum source, a negative pressure gradient is created in the interior of the receptacle so that the bodily fluid is drawn from the patient and into the suction canister via the patient conduit.

Other types of containers, such as urine collectors and chest drainage devices, can also be used to collect body fluids.

It has become important in environments such as hospitals to eliminate the handling of and thus reduce employee exposure to bodily fluids. Currently, hospitals dispose of such bodily fluid in various ways. Bodily fluid can be poured from the suction canister down the hospital sink and into the sewer system, can be incinerated as a liquid or solid, or can be disposed of at an approved hazardous waste site. If hospital employees have to handle the bodily fluid, spattering of the bodily fluid can result in hospital employees contacting the hazardous fluid.

SUMMARY OF THE INVENTION

The invention provides improved methods and apparatus for removing body fluids from patients and relates to disposing of the body fluids.

More particularly, the invention provides a suction canister including a container having a chamber for collecting fluids, a patient port, and a vacuum port. The patient and vacuum ports communicate with the chamber. When a vacuum is created in the chamber via the vacuum port, fluid is thereby drawn into the container via the patient port. The chamber is partially defined by a wall, preferably the bottom wall, including a protrusion extending into the chamber. The protrusion defines a passageway having an open outer end and a closed inner end. The protrusion includes a thin portion such that the protrusion can be broken to provide communication between the passageway and the chamber for draining fluid contained in the suction canister. Preferably, the passageway has an axis, the wall is molded with mold parts movable relative to each other in a direction parallel to the axis, and the thin portion has a reduced thickness in a direction parallel to the axis. This makes it easier to control the thickness of the thin portion during molding, because it is easier to control the relative positions of the mold parts in the direction of parting than in other directions. The invention preferably also provides a drainage device for breaking the thin portion of the protrusion and draining the canister.

The invention also provides a method of removing body fluids from a patient and disposing of the body fluids. The method includes the steps of providing a molded suction canister including a molded-in drain, providing a drainage device for automatically opening the molded-in drain and draining the contents of the suction canister, collecting body fluids in the suction canister, connecting the suction canister to the drainage device, and operating the drainage device so that the drainage device opens the drain and drains the contents of the suction canister.

The invention also provides another method of removing body fluids from a patient and disposing of the body fluids, the method comprising the steps of providing a container including a bottom wall having therein a drain, providing a drainage device for automatically opening the drain and draining the contents of the container, collecting body fluids in the container, placing the container on the drainage device, and operating the drainage device so that the drainage device opens the drain and drains the contents of the container. The drain can either be integrally molded with the container or provided by a plug closing an opening in the container.

The invention provides a suction canister or container that is easily drained of potentially hazardous fluid without contact with the fluid. The suction canister when used in conjunction with the drainage device allows a convenient means of disposing of the fluid content.

The invention provides an apparatus and method for draining bodily fluids from a container that includes positioning a container having bodily fluids therein on a support area of a drainage device, creating a vacuum in the support area to hold the container in place and operating the drainage device to alter the container to drain the bodily fluid from the container.

The invention provides an apparatus and method for draining bodily fluid from a container including positioning such a container on a support area of a drainage device, moving a cam assembly in the drainage device to a first position wherein a vacuum is created in the support area to hold the container in place and moving the cam assembly to a second position wherein a tool of the drainage device alters the container to release the bodily fluid from the container.

The invention provides an apparatus and method for draining bodily fluid from two differing types of containers holding bodily fluid, such as a suction canister and a chest fluid container. The invention includes a first support area for removably supporting the first type of container, a second support area for removably supporting the second type of container, a first inlet that communicates with and accepts bodily fluid drained from the first type of container, a second inlet that communicates with and accepts bodily fluid drained from the second type of container, and a vacuum generator for creating a vacuum at the first and second inlets.

Other features and advantages of the invention will become apparent to those of ordinary skill in the art upon review of the following description, claims and drawings.

BRIEF DESCRIPTION OF THE DRAWINGS

FIG. 1 is perspective view of an apparatus embodying the invention;

FIG. 2 is a partial sectional view of the suction canister and the drainage device;

FIG. 3 is a view similar to FIG. 2 with the suction canister connected to the drainage device;

FIG. 4 is a view taken along line 4—4 of FIG. 3;

FIG. 5 is a view similar to FIG. 3 with the tool of the drainage device breaking the protrusion of the suction canister;

FIG. 6 is a view similar to FIG. 2 showing an alternative construction and mold parts;

FIG. 7 is view taken along line 7—7 in FIG. 6;

FIG. 8 is a partial sectional view of the drain of a container that is a second alternative embodiment of the invention;

FIG. 9 is a view similar to FIG. 8 showing the drain being opened;

FIG. 10 is a partial sectional view of the drain of a container that is a third alternative embodiment of the invention;

FIG. 11 is a view similar to FIG. 10 showing the drain being opened;

FIG. 12 is a partial sectional view of the drain of a container that is a fourth alternative embodiment of the invention;

FIG. 13 is a view similar to FIG. 12 showing the drain being opened;

FIG. 14 is a partial sectional view of the drain of a container that is a fifth alternative embodiment of the invention;

FIG. 15 is a view taken along line 15—15 in FIG. 14;

FIG. 16 is a view similar to FIG. 14 showing the drain being opened;

FIG. 17 is a partial sectional view of the drain of a container that is a sixth alternative embodiment of the invention;

FIG. 18 is a view similar to FIG. 17 showing the drain being opened;

FIG. 32 is an exploded perspective view of a canister valve subassembly;

FIG. 33 is a perspective view of the canister valve subassembly, a canister cam subassembly, and the drain block subassembly;

FIG. 36 is a bottom perspective view of the canister casting assembly;

FIG. 37 is a exploded view of a portion of the second drainage device;

FIG. 38 is an exploded view of the second drainage device with a chest fluid container;

Figure 19:
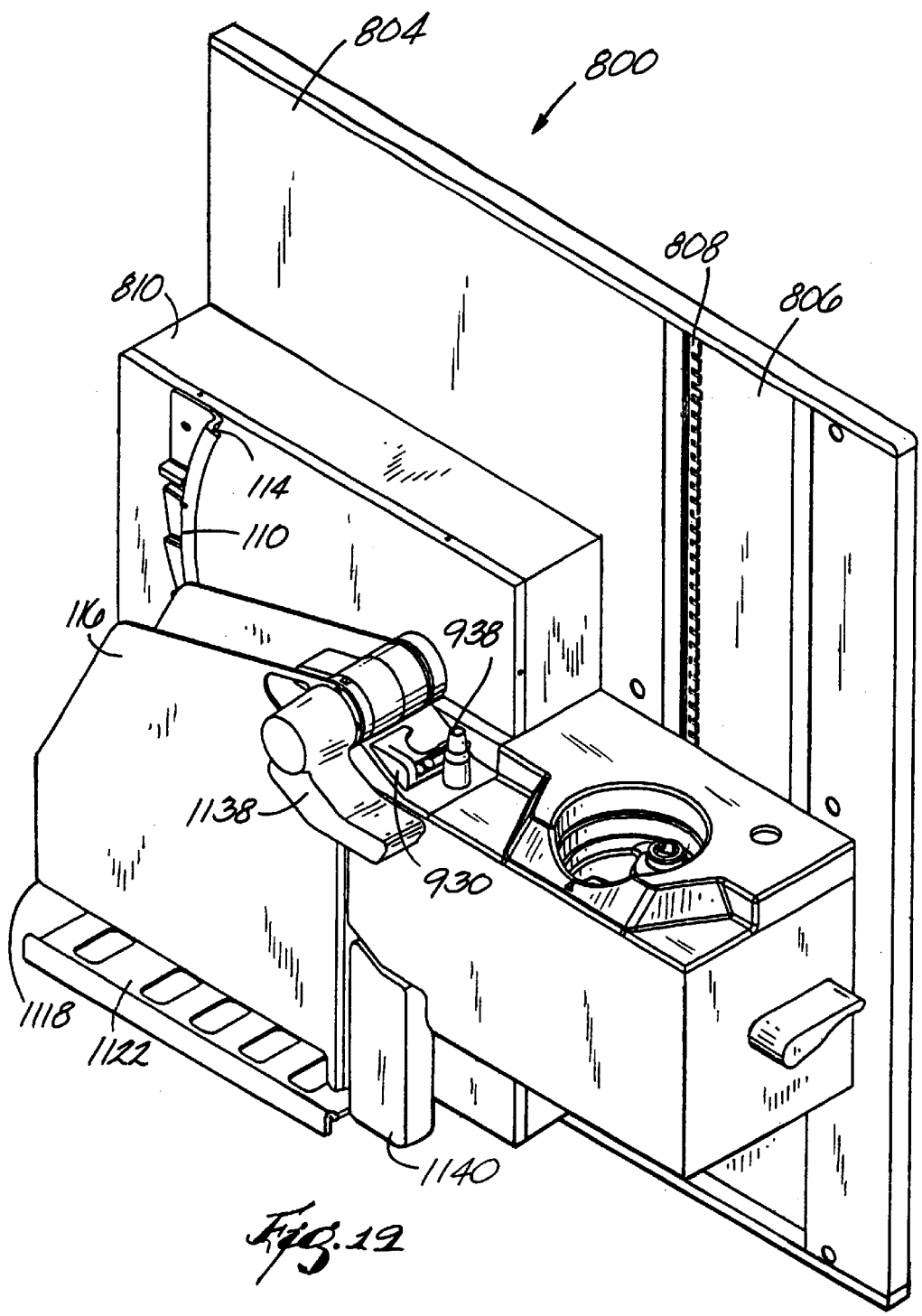
FIG. 19 is a perspective view of a second embodiment of the drainage device.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF THE PREFERRED EMBODIMENT

Referring now to the drawings in which like reference numerals refer to like parts throughout the views, there is shown in FIGS. 1 through 5 an apparatus 5 embodying the invention. The apparatus comprises a suction canister 10. The suction canister includes a container 14 which defines a chamber 18 for collecting drained fluid. The container 14 is preferably plastic (such as clear polystyrene) and is injection molded. The container 18 has an open upper end 22 and a closed lower end 26. The container 18 is defined by an annular side wall 30 and by a bottom wall 34. The bottom wall 34 includes a molded-in drain formed by a protrusion 38 extending into the chamber 18. By "molded-in" it is meant that the container 14 and the drain are formed in a single injection molding process.

As best shown in FIG. 2, the protrusion 38 defines a passageway 42 that tapers upwardly and has an open lower or outer end 46 and a blind or closed upper or inner end 50. More particularly, the protrusion 38 includes a first wall portion 54. The first wall portion 54 defines the outer end 46 of the passageway 42. As shown in FIG. 2, the first wall portion 54 is not uniform in height throughout its entire circumference due to a curvature of the bottom wall 34. However, it should be noted that the first wall portion 54 can be uniform in height throughout its circumference. Further, the height of the first wall portion 54 is preferably minimized to minimize the volume of fluid that remains in the suction canister 10 after it has been drained.

The protrusion 38 also includes a second wall portion 58 that defines the closed inner end 50 of the passageway 42. The second wall portion 58 defines an outwardly or downwardly opening, non-circular socket 62 at the inner end 50 of the passageway 42 as best shown in FIGS. 2 and 4. The socket is preferably hexagonal.

Referring now to FIG. 2, a thin or frangible wall portion 66 integrally connects the first wall portion 54 and the second wall portion 58. As will be explained in more detail hereafter, the frangible wall portion 66 can be broken to provide communication between the passageway 42 and the chamber 18 to enable draining of the fluid from the suction canister 10. The frangible wall portion 66 is small in size (preferably about 0.010 inch thick) to provide for ease of breakage when draining is desired yet is also strong enough to withstand the tensile and circumferential stresses when a vacuum is created in the chamber 18 when the suction canister 10 is being filled with fluid. Further, due to the placement and configuration of the frangible wall portion 66 and the socket 62, inadvertent breaking of the protrusion 38 is minimized.

As shown in FIG. 1, the suction canister 10 also includes a lid 70 which closes the upper end 22 of the container 14. The lid 70 has therein a patient port 74 which communicates with the chamber 18. Extending upwardly from the patient port is a patient port wall 78. To enable communication between the fluid to be drained and the patient port 74, a patient conduit 82 is affixed to the patient port wall 78 by forcing one end 86 of the patient conduit 82 over the patient port wall 78. The other end 90 of the patient conduit 82 communicates with the fluid to be drained such as in a patient cavity 94. When the patient conduit 82 is not attached to the patient port wall 78, a cap (not shown) can be placed over the patient port wall 78 to prevent any fluid from leaking from the suction canister 10.

The lid 70 of the suction canister 10 also includes a vacuum port 98 which communicates with the chamber 18 via a filter (not shown). The filter can be, for example, a hydrophobic filter. Extending upwardly from the vacuum port 98 is a vacuum port wall 102. To enable a vacuum to be created in the chamber 18 of the suction canister 10, the vacuum port 98 communicates with a vacuum source 106 via a suction conduit 110. The suction conduit 110 is affixed to the vacuum port wall 102 by forcing one end 114 of the suction conduit 110 over the vacuum port wall 102. The other end 118 of the suction conduit 110 is placed in communication with the vacuum source 106. The filter prevents contamination of the vacuum source 106. When the suction conduit 110 is not attached to the vacuum port wall 102, a cap (not shown) can be placed over the vacuum port wall 102 to prevent any fluid from leaking from the suction canister 10.

The suction canister 10 is used in the collection of fluids as follows. One end 114 of the suction conduit 110 is affixed to the vacuum port wall 102 as previously described and the other end 118 is placed in communication with the vacuum source 106. One end 86 of the patient conduit 82 is affixed to the patient port wall 78 as previously described and the other end 90 is placed in communication with the fluid to be drained such as in the patient cavity 94. When the vacuum source 106 is on, a vacuum is created in the chamber 18 of the container 14 such that fluid is drawn from the patient cavity 94, through the patient conduit 82 and into the container 14 via the patient port 74.

When the container 14 is filled with fluid or fluid no longer needs to be collected, the patient conduit 82 and the suction conduit 110 can be detached from the lid 70 of the suction canister 10. The caps can then be placed on the patient port wall 78 and the vacuum port wall 114 as previously described to prevent fluid from leaking from the container 14. The suction canister 10 can then be stored until the suction canister is to be drained of its fluid contents.

The apparatus 5 also comprises a drainage device 122 with an upwardly tapered drain conduit 126 and a movable tool 130 as shown in FIG. 1. Preferably, the drainage device 122 uses water pressure and a venturi to create a vacuum that suctions the fluid from the container 14 and delivers this fluid directly to the sanitary sewer line. The drainage device 122 can include a device such as the Deknatel EDUCTOR™ manufactured by Deknatel, Inc. of Fall River, Massachusetts. A suitable drainage device is also disclosed in U.S. Pat. No. 5,217,038, which is incorporated herein by reference.

To enable the fluid in the container 14 to be drained, the drainage device 122 breaks the protrusion 38 as follows. When a suction canister 10 needs to be drained, the suction canister 10 is placed onto the drainage device 122 so that the drain conduit 126 of the drainage device 122 is inserted into the passageway 42 of the suction canister 10 as shown in FIG. 3. The drain conduit 126 has a configuration that is complementary to the passageway 42. A friction fit between the drain conduit 126 and the first wall portion 54 of the suction canister 10 provides a fluid seal. When the drain conduit 126 is fully wedged into the passageway 42 and the seal formed, the tool 130 is extended upwardly from the drainage device 122 and into the socket 62 of the passageway 42 as shown in FIG. 3. The tool 130 has a configuration that is complementary to that of the socket 62. Referring now to FIG. 5, further upward movement of the tool 130 (as depicted by arrow A) in conjunction with rotational movement of the tool 130 (as depicted by arrow B) breaks the frangible wall portion 66 of the protrusion 38, thereby disconnecting the second wall portion 58 from the first wall portion 54. The breakage of the protrusion 38 allows the fluid within the container 14 to exit the chamber 18 and enter the drainage device 122 via the drain conduit 126. As shown by the small arrows in FIG. 5, the fluid flows through the conduit 126 around the tool 130. The seal between the drain conduit 126 and the first wall portion 54 of the protrusion 38 prevents fluid from flowing anywhere but through the passageway 42 and into the drainage device 122.

During drainage of the fluid from the suction canister 10, the caps on the patient port wall 78 and/or the vacuum port wall 102 can be removed to vent the chamber 18 to aid in drainage of the fluid. Alternatively, a vent could be provided in the drainage device 122 to aid in drainage of the fluid from the suction canister 10.

An apparatus 200 which is a first alternative embodiment of the invention is illustrated in FIGS. 6 and 7. Except as described below, the apparatus 200 is identical to the apparatus 5, and common elements have been given the same reference numerals.

The apparatus 200 comprises a suction canister 210 including a container 214. The container 214 is preferably made of clear polystyrene. The passageway 42 has an axis 226, and the container 214 is preferably injection molded using mold parts 218 and 222 which are movable relative to each other or part in the direction of the axis 226. In other words, the mold parts 218 and 222 part vertically as shown in FIG. 6. This is identical to the manner in which the container 14 shown in FIGS. 1–5 is preferably molded.

It has been found that it can be difficult to control the thickness of the thin wall portion 66 of the container 14 because it can be difficult to precisely maintain the relative horizontal positions of the mold parts during molding. Any sideways or horizontal movement of one mold part relative to the other can have a significant effect on the thickness of the thin wall portion 66, because the wall portion 66 has a reduced thickness in the horizontal direction. On the other hand, it is relatively easy to maintain the relative vertical positions of the mold parts, i.e., the spacing of the mold parts in the direction of parting.

For this reason, the container 214 has a thin wall portion 266 with a reduced thickness in the direction of parting of the mold parts 218 and 222, i.e., in the vertical direction in FIG. 6. Viewed another way, the thin wall portion 266 has a reduced thickness in a direction parallel to the axis 226. The thickness of the wall portion 266 is preferably 0.010 inch, and can be relatively easily controlled. The wall portion 266 also has a radial or horizontal dimension that is substantially greater than the reduced thickness. This radial dimension is preferably approximately 0.060 inch. Variation of this dimension during molding is not critical. The thin wall portion 266 is easily broken when draining is desired yet is also strong enough to withstand the stress of a vacuum in the chamber 18. In fact, it has been found that the thin wall portion 266 can be broken simply by pushing upwardly on the second wall portion 58. It is not necessary to twist the wall portion 58 in order to break the wall portion 266.

The container 214 also differs from the container 14 in that the socket 62 is star-shaped rather than hexagonal. Obviously, any non-circular shape can be employed.

It should be noted that the bottom wall of the container could be conical or sloped toward the drain for improved drainage.

An apparatus 300 which is a second alternative embodiment of the invention is illustrated in FIGS. 8 and 9. Except as described below, the apparatus 300 is identical to the apparatus 5, and common elements have been given the same reference numerals.

The apparatus 300 comprises a container 305 with a bottom wall 309 having therein an opening 313 closed by a plug 317 inserted in the opening 313. The plug 317 is preferably made of an elastomer or thermoplastic and snaps into the opening. The plug has therein a blind central passageway 321 with a closed upper end 325. As shown in FIG. 9, the drainage device 122 includes a pointed conduit or hollow needle 329 that pierces the upper end 325 of the passageway 321 so that fluid flows out of the container 305 through the needle or conduit 329.

An apparatus 400 which is a third alternative embodiment of the invention is illustrated in FIGS. 10 and 11. Except as described below, the apparatus 400 is identical to the apparatus 5, and common elements have been given the same reference numerals.

The apparatus 400 comprises a container 405 with a bottom wall 409 having therein an opening 413 closed by a plug 417 inserted in the opening 413. The plug 417 is preferably made of an elastomer or thermoplastic and snaps into the opening. As shown in FIG. 11, the drainage device 122 includes a conduit 429 with a closed upper end and side openings 433. The conduit 429 pushes the plug up into the container 405 so that fluid flows out of the container 405 through the openings 433 and into the conduit 429.

An apparatus 500 which is a fourth alternative embodiment of the invention is illustrated in FIGS. 12 and 13. Except as described below, the apparatus 500 is identical to the apparatus 5, and common elements have been given the same reference numerals.

The apparatus 500 comprises a container 505 with a bottom wall 509 having therein an opening 513 closed by a plug 517 inserted in the opening 513. The plug 517 is preferably made of a thermoplastic and snaps into the opening. The plug has therein a blind central passageway 521 with a closed lower end 525. As shown in FIG. 13, the drainage device 122 includes a pointed conduit or hollow needle 529 that pierces the lower end 525 of the passageway 521 so that fluid flows out of the container 505 through the needle or conduit 529.

An apparatus 600 which is a fifth alternative embodiment of the invention is illustrated in FIGS. 14–16. Except as described below, the apparatus 600 is identical to the apparatus 5, and common elements have been given the same reference numerals.

The apparatus 600 comprises a container 605 with a bottom wall 609 having therein an internally threaded opening 613 closed by a plug 617. The plug 617 is preferably made of a thermoplastic and threads into the opening 613. As shown in FIG. 15, the plug has a hexagonal head 621. As shown in FIG. 16, the drainage device 122 includes a tool 629 with a socket 633 that engages the plug head 621 and unthreads the plug 617 from the opening 613 so that fluid flows out of the container 605 through the opening 613.

An apparatus 700 which is a sixth alternative embodiment of the invention is illustrated in FIGS. 17 and 18. Except as described below, the apparatus 700 is identical to the apparatus 5, and common elements have been given the same reference numerals.

The apparatus 700 comprises a container 705 with a bottom wall 709 having therein an opening 713 closed by a plug 717. The plug 717 is preferably made of a thermoplastic and is glued, ultrasonically welded or otherwise secured over the opening. The plug 717 has a construction similar to the bottom wall of the container 214 shown in FIGS. 6 and 7. Thus, the plug 717 has a first wall portion 54, a second wall portion 58 and a frangible wall portion 266 like those of the suction canister 210. As shown in FIG. 18, the drainage device 122 includes a conduit 729 with a closed upper end and side openings 733. The conduit 729 breaks the thin wall portion 721 and extends into the container 705 so that fluid flows out of the container 705 through the openings 733 and into the conduit 729.

Turning now to FIG. 19, there is shown a second embodiments of the drainage device 800. The drainage device 800 is designed to drain two differing types of bodily fluid containers, such as, for example, a suction canisters 10 (FIG. 40) and chest fluid containers 802 (shown in phantom in FIG. 38), such as the Pleur-Vac™ container from Deknatel. However, other types of containers can also be used with the invention.

Figure 20:
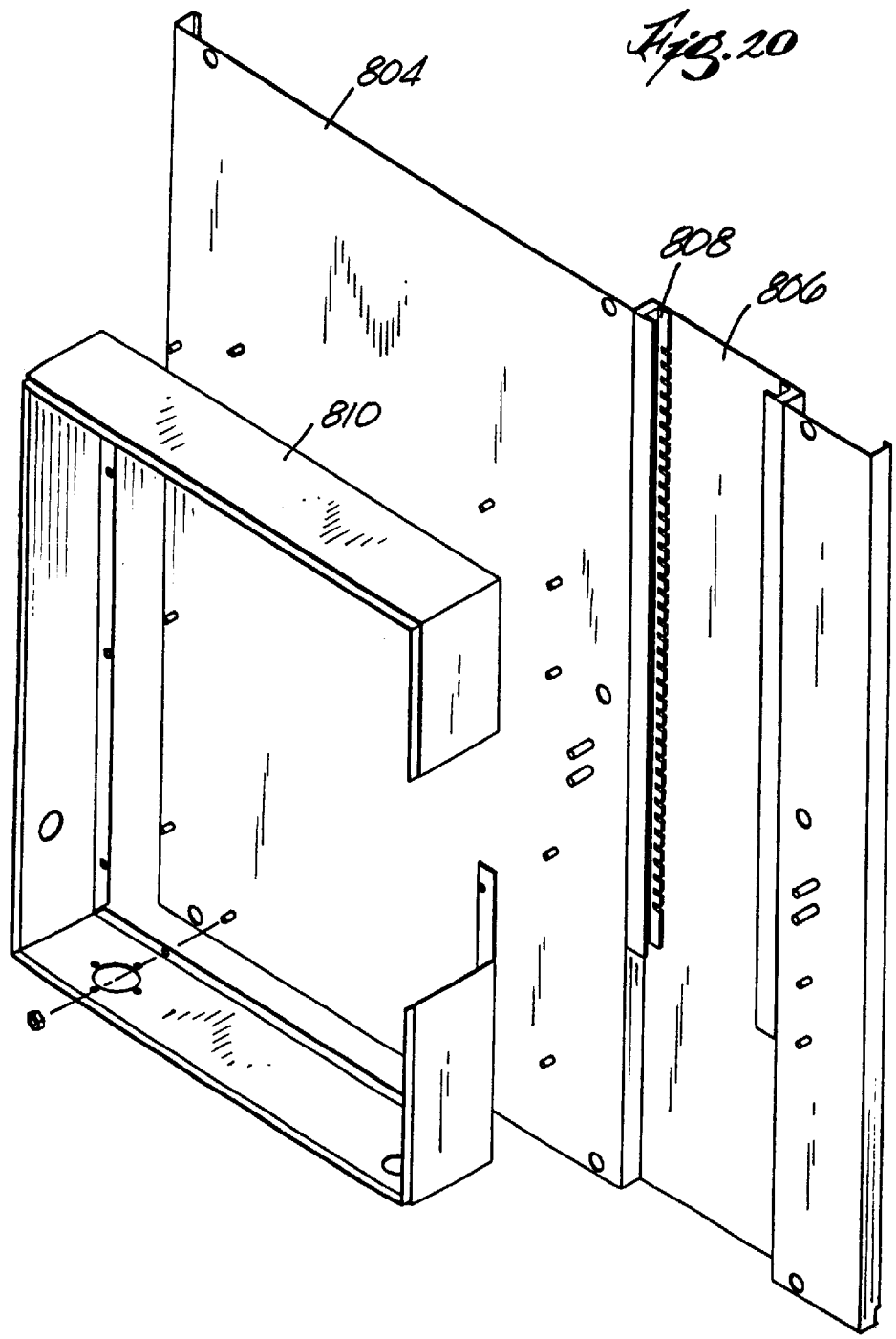
FIG. 20 is a perspective view of the back plate and frame of the second drainage device.

As is best shown in FIG. 20, the drainage device 800 includes a mounting plate 804 that is adapted to be mounted to a vertical surface, such as a wall in an operating suite. The plate 804 includes a channel 806 having a bracket track 808. A main enclosure frame 810, which is generally C-shaped, is mounted to the plate 804.

Figure 21:
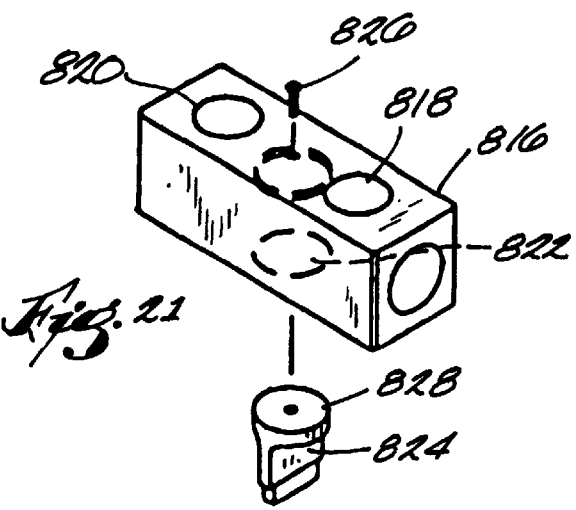
FIG. 21 is an exploded perspective view of a manifold of the second drainage device.
Figure 22:
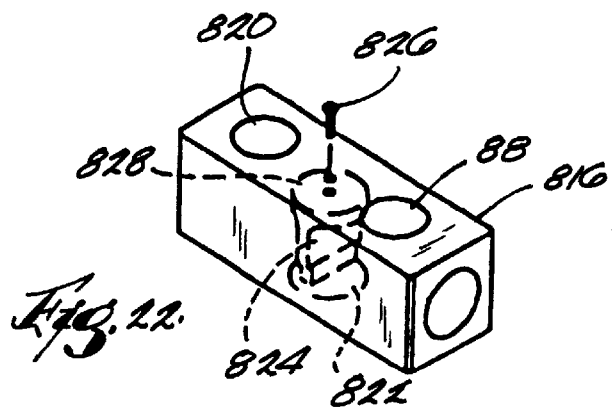
FIG. 22 is a perspective view of the manifold.
Figure 23:
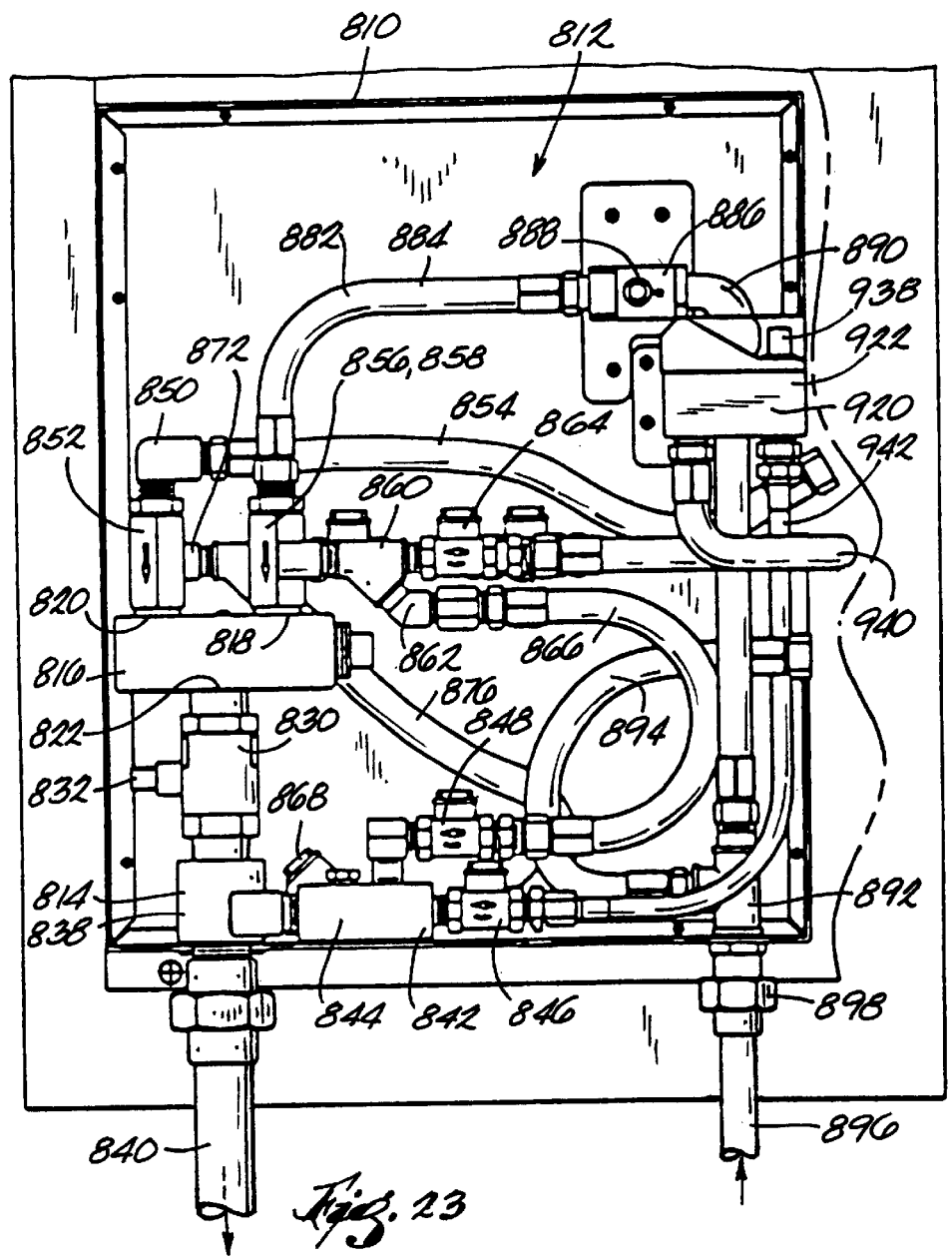
FIG. 23 is a front view of a plumbing assembly of the second drainage device.

Turning now to FIGS. 21–23, the drainage device 800 includes a plumbing assembly 812 that is housed in the frame 810. The plumbing assembly 812 includes a plurality of plumbing subassemblies.

The first subassembly 814 includes a manifold 816, which is preferably a Y-type manifold having two inlet ports 818, 820 and one outlet port 822. A T-divider 824 is positioned centrally within the manifold 816 to prevent communication between the two inlet ports 818 and 820. The T-divider 824 is mounted in position using a screw 826 and a top mounted gasket 828. A ball valve 830 is connected to the outlet port 822 of the manifold 816. The ball valve 830 has an output shaft 832. An arm 834 is connected to the shaft 832 and a handle 836 is connected to the arm 834 (FIG. 37). Rotation of the handle 836 turns the valve on and off. A connector 838 is attached to the valve 830. The connector 838 is connected to a drain pipe 840 which is preferably in communication with a sanitary sewer line.

A second plumbing subassembly 842 includes a manifold 844 connected to the connector 838. A swing check valve 846 is connected to the manifold 842 and a swing check valve 848 is connected to the manifold 844.

A third plumbing subassembly 850 includes a vacuum generator or venturi valve 852 connected to the inlet port 820 of the manifold 816. A hose 854 is connected to the venturi valve 852.

A fourth plumbing subassembly 856 includes a vacuum generator or venturi valve 858 that is connected to the inlet port 818 of the manifold 816.

A fifth plumbing subassembly 860 includes a Y fitting 862 that is connected to the venturi valve 858. A swing check valve 864 is attached to one leg of the Y fitting 862 and a hose 866 is attached to the other leg of the Y fitting 862. The other end of the hose 866 is connected to the check valve 848 of the second plumbing subassembly 842.

Figure 24:
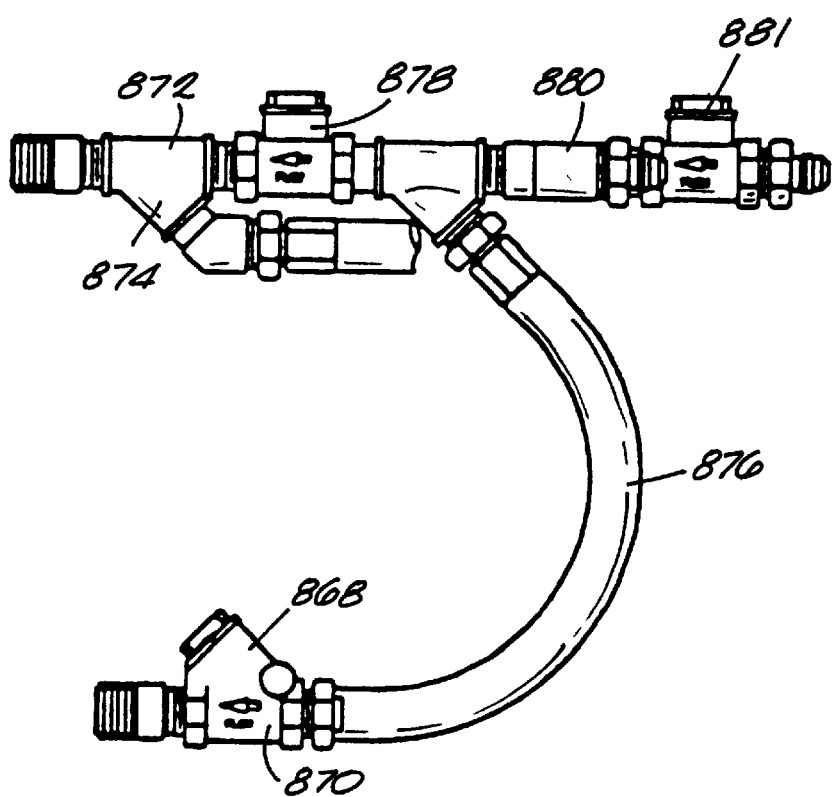
FIG. 24 is a front view of the sixth and seventh plumbing subassemblies that are hidden from view in FIG. 23.

A sixth plumbing subassembly 868, as best shown in FIG. 24 since it is partially hidden from view in FIG. 23, includes a Y-pattern check valve 870 that is connected to the connector 838 of the first plumbing subassembly 814.

A seventh plumbing subassembly 872, as best shown in FIG. 24 since it is partially hidden from view in FIG. 23, includes a Y fitting 874 that is connected to the venturi valve 858. A hose 876 is extends between on leg of the Y fitting 874 and the check valve 870 of the sixth plumbing subassembly 868. A swing check valve 878 is connected to the other leg of the Y fitting 874. A Y fitting 880 is connected to the swing check valve 878. A check valve 881 is connected to one leg of the Y fitting 880.

An eighth plumbing subassembly 882 includes a hose 884 extending between the venturi valve 858 and a ball valve 886. The ball valve 886 has an output shaft 888, rotation of which turns the ball valve 886 on and off. A hose 890 extends between the ball valve 886 and a tee 892. A hose 894 extends from one leg of the tee 892. A water source 896 is connected to the tee 892 via the fitting 898.

Figure 26:
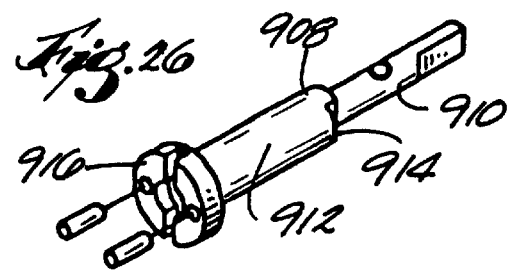
FIG. 26 is a perspective view of a shaft pin of the swingarm drive assembly.
Figure 25:
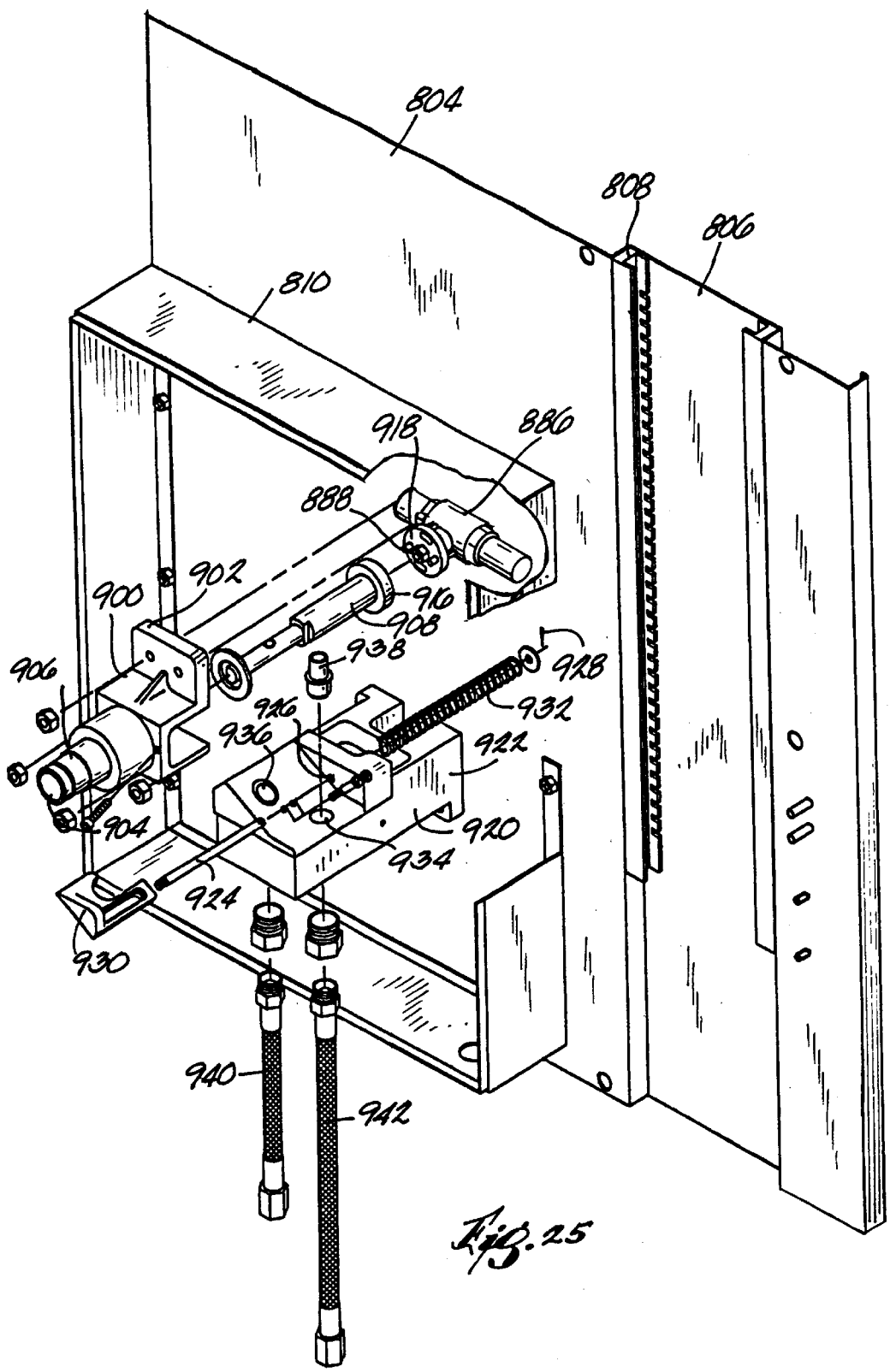
FIG. 25 is an exploded perspective view of a swingarm drive assembly and a port block assembly mounted within the frame.

With reference to FIG. 25, a swingarm drive assembly 900 is positioned within the frame 810. The assembly 900 includes shaft collar 902 that houses a shaft bearing 904 within a bearing sleeve 906. The collar 902 is mounted to the plate 804. A shaft pin 908, as best shown in FIG. 26, is positioned within the bearing 904. The shaft pin 908 includes a first portion 910 and a second portion 912 that are separated by a shoulder 914. The second portion 912 terminates in a disk 916. The disk 916 mates with a drive disk 918 that is mounted to the output shaft 888 of the ball valve 886. Rotation of the shaft pin 908 opens and closes the ball valve 886.

Continuing to refer to FIG. 25, a port block assembly 920 is positioned within the frame 810. The port block assembly 920 includes a port block 922 that is mounted to the plate 804 such that the hose 890 can pass vertically behind the block 922. A threaded pin 924 is housed in a bore 926 such that the ends of the pin 924 extend from the bore 926. A cotter pin 928 extends through one end and a lever 930 is threaded onto the other end. A spring 932 surrounds the pin 924. The block 922 has therein two inlet ports 934 and 936. A connector 938 extends upwardly from the inlet port 934. The lever 930 in its spring biased position covers the inlet port 936. To expose the inlet port 936, the lever 930 is pulled horizontally away from the block 922.

The block 922 further includes two outlets which are hidden from view in FIG. 25. As shown in FIG. 23, a hose 940 extends between one of the outlets and the check valve 864 of the fifth plumbing subassembly 860, and a hose 942 extends between the other outlet and the check valve 846 of the second plumbing subassembly 842.

Figure 27:
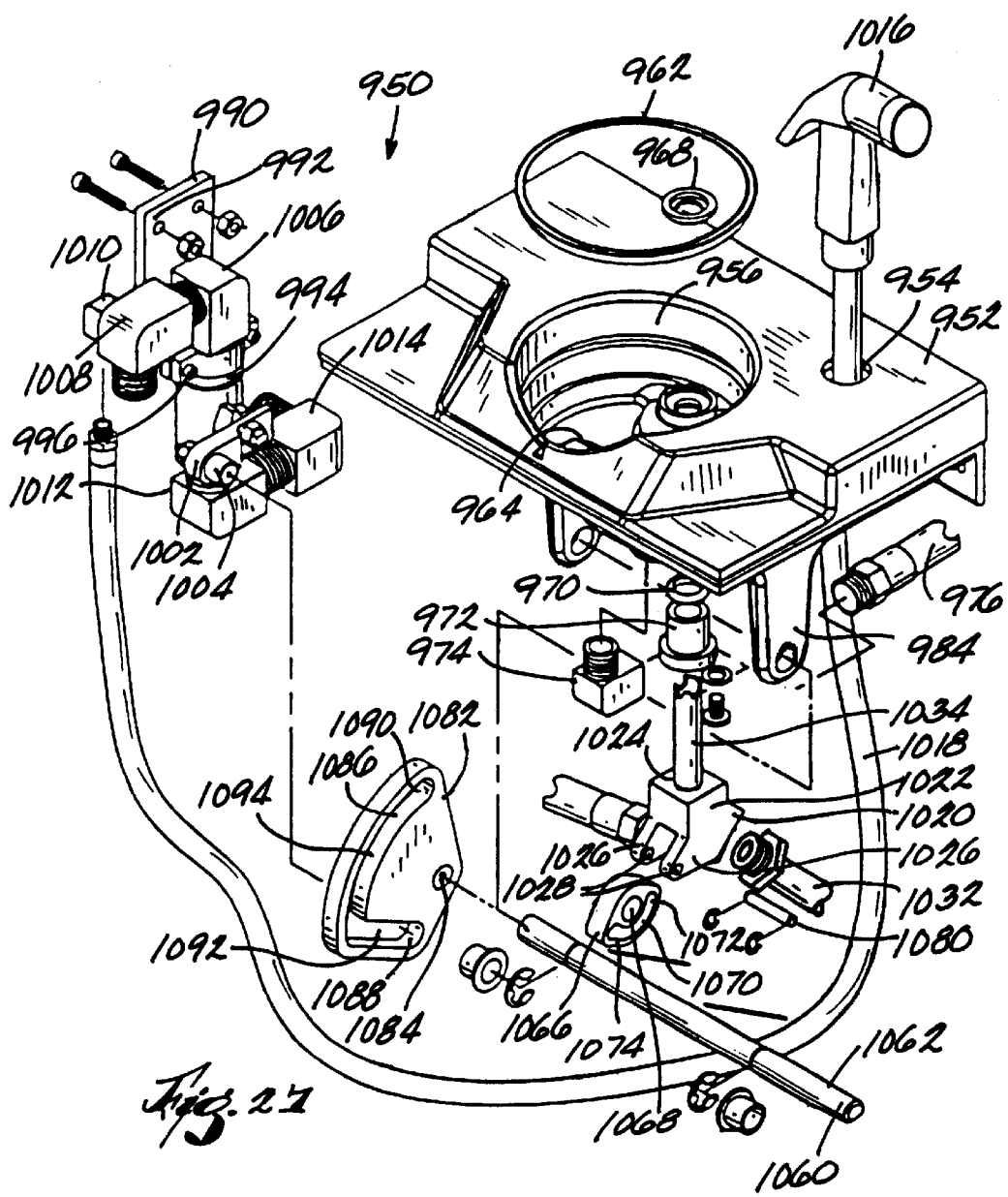
FIG. 27 is an exploded perspective view of a canister casting assembly of the second drainage device.
Figure 28:
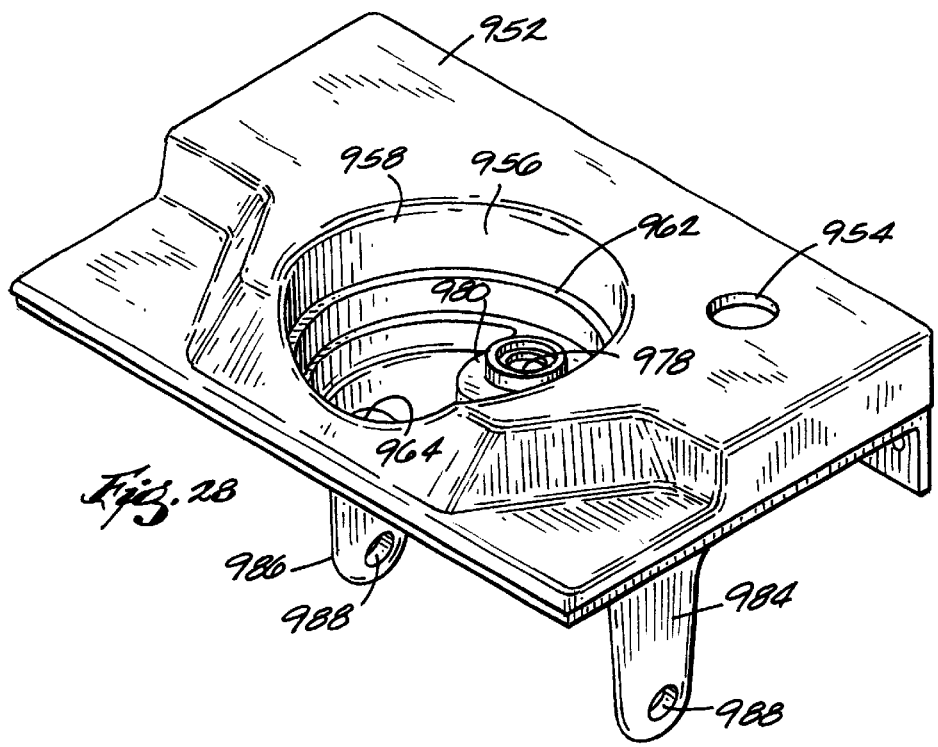
FIG. 28 is a perspective view of a canister casting.
Figure 29:
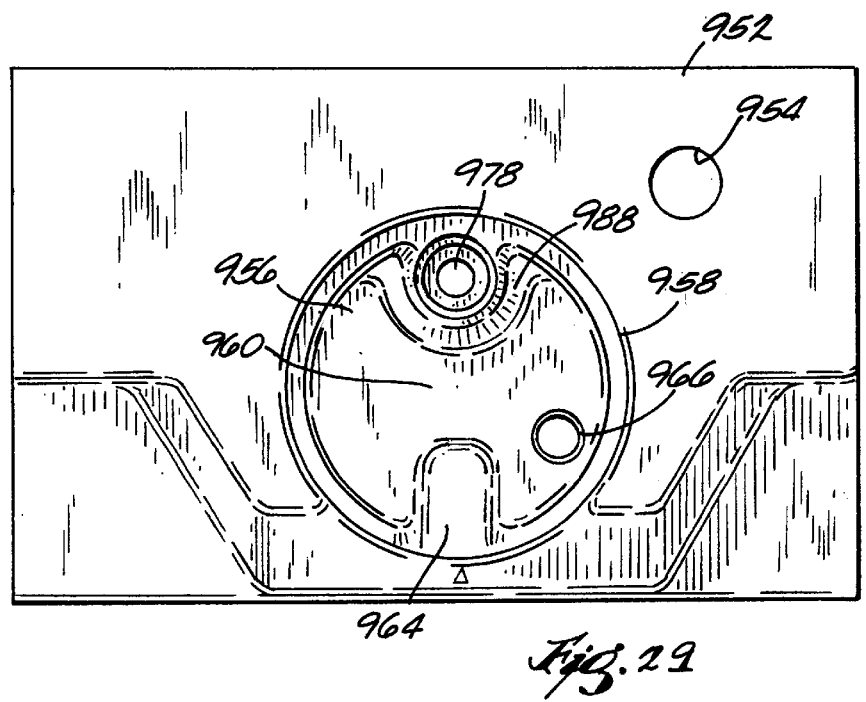
FIG. 29 is a plan view of the canister casting.
Figure 30:
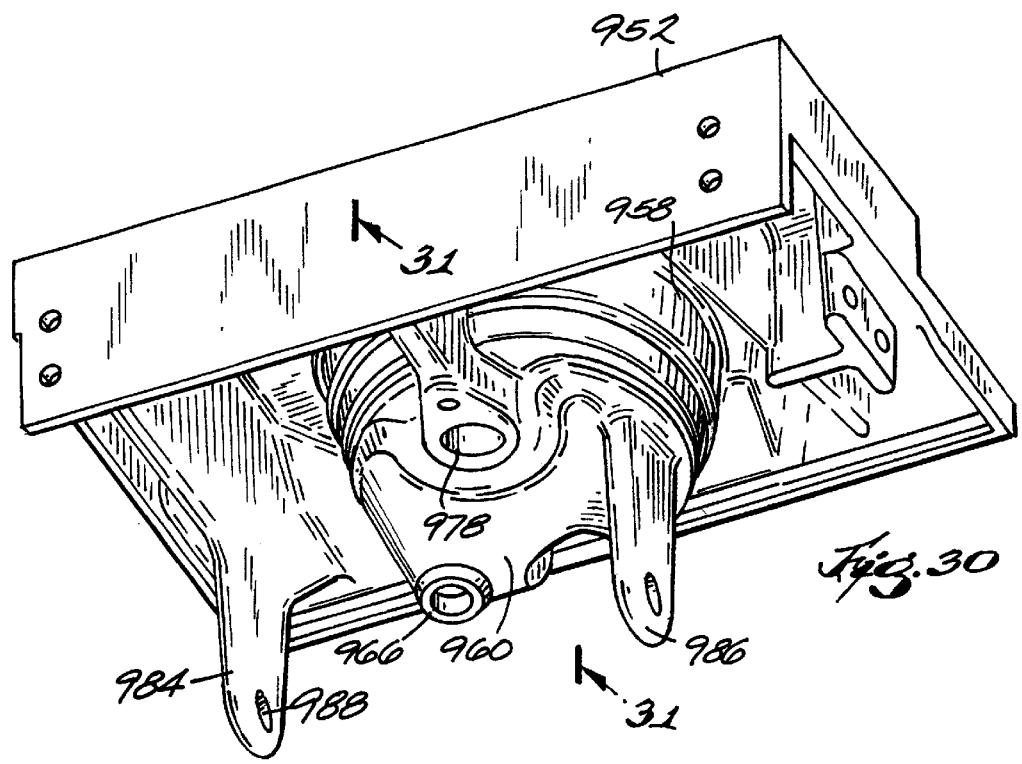
FIG. 30 is a bottom perspective view of the canister casting.
Figure 31:
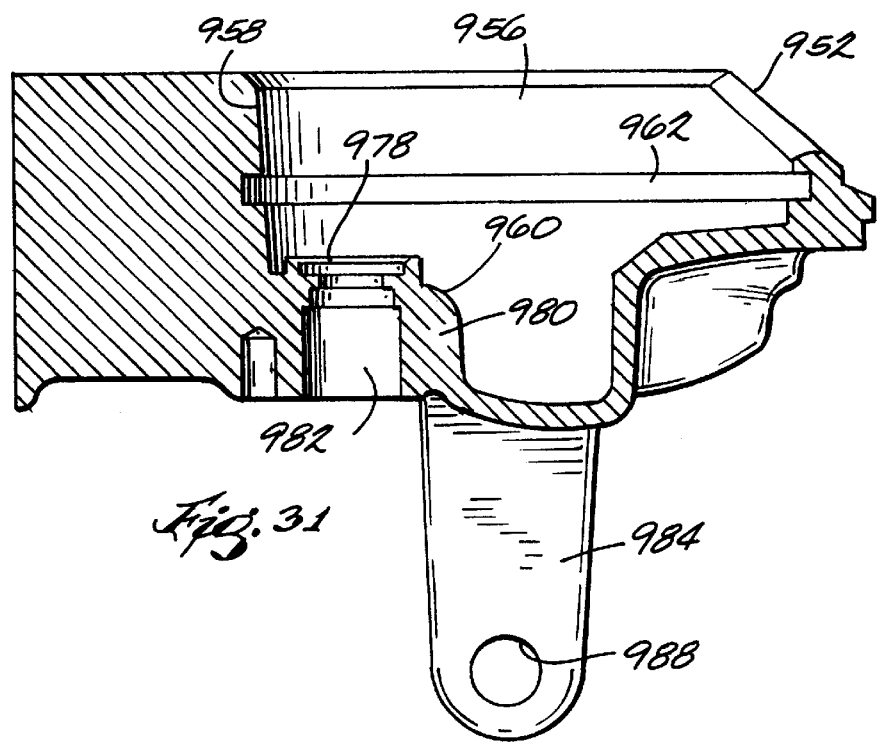
FIG. 31 is a view taken along line 31—31 of FIG. 30.

Turning now to the canister draining portion of the drainage device 800, a canister casting assembly 950 is shown in FIGS. 27 and 36. The assembly 950 includes a casting 952 as is best shown in FIGS. 28–31. The casting 952 includes an aperture 954 and a container support area such as central recess 956, both in a top surface of the casting 952. It should be noted that the support area could have other configurations to removably support the suction canister.

The recess 956 is designed to house and support a suction canister 10. The recess 956 is defined by an annular wall 958 and a bottom wall 960. A lip seal 962 is housed in the wall 958, and preferably housed in a groove in the wall 958 to prevent dislodging as suction canisters are inserted and removed from the recess 956. The seal 962 provides a fluid-tight seal when a suction canister 10 is being drained to prevent any fluid draining from the suction canister 10 from contacting the user.

A key 964 extends inwardly from the wall 958. The key 964 cooperates with a keyway in the suction canister 10 so as to properly oriented the suction canister 10 relative to the casting 952. A suction port 966 is provided for in the bottom wall 960. As best shown in FIG. 27, an elbow 974 is placed in communication with the suction port 966 and a hose 976 extends between the elbow 974 and the check valve 881 of the seventh plumbing subassembly 872.

A drain port 978 is also provided in the bottom wall 960 on a raised portion 980 of the bottom wall 960 that is spaced from the suction port 966. A gasket 968 is positioned above the drain port 978. A drain passageway 982 is provided in the casting 952 in communication with the drain port 978. A gasket 970 and a sleeve 972 are housed in the passageway 982. The casting 952 includes two downwardly extending legs 984 and 986 that have therein axially aligned apertures 988.

The canister casting assembly 950 includes a canister valve subassembly 990 as best shown in FIGS. 32 and 33. This subassembly 990 includes a valve bracket 992 that is attached to the casting 952 (FIGS. 36 and 37). A ball valve 994 is secured to the bracket 992 with a pair of pipe hangers 996. The ball valve has an output shaft 998. A valve handle 1002 is secured to the output shaft 998. A cam follower 1004 is secured to the handle 1002. An elbow fitting 1006 is attached to one end of the ball valve 994, an elbow fitting 1008 is attached to the elbow fitting 1006, and an elbow fitting 1010 is attached to the elbow fitting 1008. An elbow fitting 1012 is attached to the other end of the ball valve 994, and an elbow fitting 1014 is attached to the elbow fitting 1012.

Referring back to FIG. 27, a manual sprayer 1016 is positioned in the aperture 954 of the casting 952. A hose 1018 extends between the sprayer 1016 and the elbow 1010. The hose 854 of the third plumbing subassembly 850 is connected to the elbow 1008 and the hose 894 of the eighth plumbing subassembly 882 is attached to the elbow 1014.

Referring now to FIGS. 27 and 33, a drain block assembly 1020 is shown. The drain block assembly 1020 includes a 45° pipe block 1022 defining a central passageway 1024. The block 1022 has two legs 1026 having therein axially aligned apertures 1028. A hose 1032 extends between one end of the passageway 1024 and the other leg of the Y fitting 880 of the seventh plumbing subassembly 872.

Figure 35:
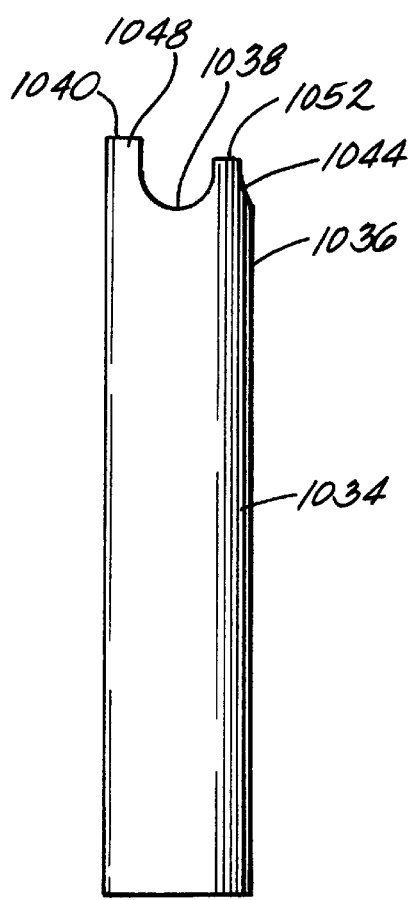
FIG. 35 is a side elevational view of the drain pipe.
Figure 34:
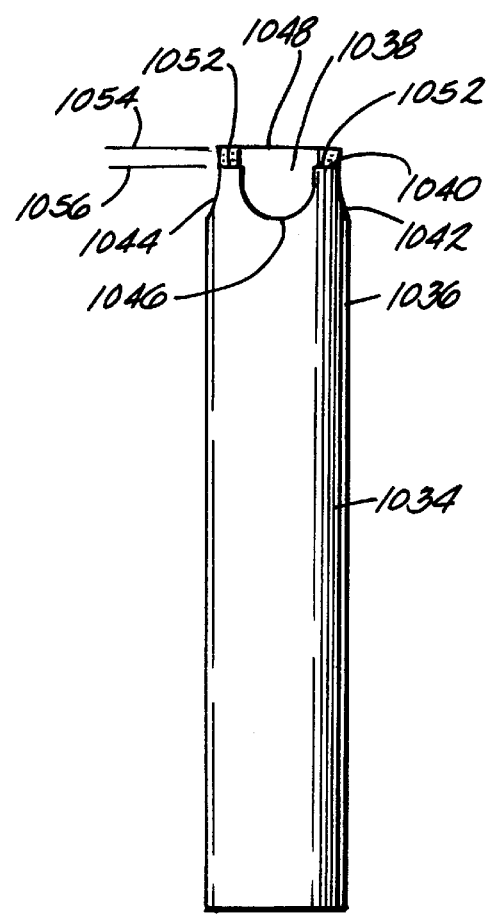
FIG. 34 is a front elevational view of a drain pipe.

A tool or opener, such as drain pipe 1034, is in communication with the other end of the passageway 1024. As is best shown in FIGS. 34 and 35, the drain pipe 1034 includes a cylindrical wall 1036 which defines a central passageway 1038. The wall 1036 terminates in an end surface 1040 such that the passageway 1038 is accessible from the end surface 1040.

The drain pipe 1034 has therein three generally U-shaped recesses 1042, 1044, 1046 in the wall 1036 and adjacent the end surface 1040. A first portion 1048 of the wall 1036 is located between the recess 1042 and the recess 1044. A second portion 1052 of the wall 1036 is located between the recess 1044 and the recess 1046. A third portion 1052 of the wall 1036 is located between the recess 1046 and the recess 1042. Preferably, the first portion 1048 includes more of the circumference of the end surface 1040 of the wall 1036 than do the second or third portions, 1050 and 1052 respectively.

The first portion 1048 does not terminate in a common plane with the second or third portions 1050 and 1052, respectively. Instead, the first portion 1048 terminates in a first plane 1054 and the second and third portions, 1050 and 1052, respectively terminate in a second plane 1056. The pipe drain 1034 is adapted to alter the suction canister 10 so that the bodily fluid held within the suction canister 10 can drain from the suction canister 10.

Referring to FIGS. 27 and 33, a canister cam subassembly 1060 is shown. This assembly 1060 causes the rotation of the output shaft 998 of the ball valve 994 of the canister valve subassembly 990 as well as raises and lowers the drain pipe 1034.

In particular, the canister cam subassembly 1060 includes a cam shaft 1062 that is positioned in the apertures 988 of the legs 984 and 986 of the casting 982 for rotational support. The cam shaft 1062 has one end onto which a handle 1064 is mounted (FIG. 38). The subassembly 1060 further includes a pipe cam 1066 having an aperture 1068 and an arcuate cam slot 1070. The slot 1070 has a first end 1072 and a second enlarged end 1074. The pipe cam 1066 is centrally mounted on the cam shaft 1062 such that the cam shaft 1062 is housed in the aperture 1068 and held in place with a pin 1078 (FIG. 36). The pipe cam 1066 is also positioned such that the legs 1026 of the pipe block 1022 are adjacent the pipe cam 1066. A rod 1080 extends from one leg 1026 of the pipe block 1022, through the slot 1070 of the pipe cam 1066, then to the other leg 1026 of the pipe block 1022 (FIGS. 33 and 36).

A second or overtravel cam 1082 includes an aperture 1084 and a curved cam slot 1086. The slot 1086 has a first end 1088, a second end 1090, a first portion 1092 and a second portion 1094. The cam 1082 is mounted on the end of the cam shaft 1062 such that the cam shaft 1062 is housed in the aperture 1084. A pin secures the cam 1082 to the cam shaft 1062. The cam 1082 is positioned such that the cam follower 1004 of the canister valve subassembly 990 is positioned in the first end 1088 of the slot 1086 and can travel in the slot 1086.

Referring now to FIGS. 37 and 38, the casting assembly 950 is mounted to the plate 804 adjacent the frame 810 by securing the casting 952 to the plate 804 such as with fasteners. A canister skirt cover 1102 is connected to the canister casting assembly 950 so as to shield the moving parts of the canister casting assembly 950 from the user.

A main enclosure cover 1104 is mounted to the frame 810 to cover the plumbing assembly 812. The cover 1104 includes an aperture 1106 into which the shaft pin 908 of the swingarm drive assembly 900 is positioned. The cover 1104 includes a cut out portion 1108 that abut the port block assembly 920 and allows the user access to the lever 930 and the connector 938. The cover 1104 has thereon an arcuate swingarm track 1110. The track 1110 includes ratchet teeth 1112 and has therein a channel 1114.

Turning now to FIG. 38, the swingarm 1116 is shown. The swingarm 1116 includes a pair of generally parallel, spaced side plates 1118 and a bottom plate 1120. The plates 1118 and 1120 define a support area 1122 for supporting the chest fluid container 802. A barrel assembly 1124 extends between the plates 1118. The assembly 1124 includes a drive washer 1126, a support holder, a spring housing, a spring, and a bearing washer. The barrel assembly 1124 is supported by the shaft pin 908 of the swingarm drive assembly 900 and held in place using a shaft pin 1136.

Referring back to FIG. 19, a handle 1138 is attached to the end of the shaft pin 1136. A handle 1140 is secured to an end of the side plate 1118 with a bracket. The handle 1140 is secured to the bracket so as to be pivotable about a pin. An engager is secured to the handle 1140. The engager is positioned in and travels along the channel 1114 of the swingarm track 1110 as the swingarm 1116 is rotated.

The operation of the drainage device will now be explained for both drainage of the chest fluid containers 802 and the suction containers 10.

With reference to FIG. 19, if a user desires to drain a chest fluid container 802, the user positions the container 802 in the support area 1122 of the swingarm 1116. Typically, chest fluid containers 802 have two conduits 1150 and 1152 extending therefrom (FIG. 38). The user connects one conduit 1150 to the connector 938. The user pulls the lever 930 toward themselves thus exposing the second inlet port 936. The user secures the conduit 1152 to the inlet port 936.

The user then rotates the swingarm 1116 with the container 802 therein clockwise with reference to FIG. 19. After the swingarm 1116 has rotated approximately 90 degrees, and with reference to FIG. 23, the shaft pin 908 will have rotated sufficiently so as to turn the output shaft 888 of the ball valve 886 of the eighth plumbing subassembly 882 and turn the ball valve 886 on. With the ball valve 886 in the on position, water can flow from the water source 896, through the hose 890, through the ball valve 886, through the hose 884, through the venturi valve 858, through the manifold 816, then through the first plumbing subassembly 814 to the drain pipe 840. Water does not flow through hose 894 because the ball valve 994 of the canister valve subassembly 990 is in its off position.

After the user finishes rotating the swingarm 1116 to a desired position, the swingarm 1116 maintains its position because the engager of the handle 1140 contacts the ratchet teeth 1112 of the swingarm track 1110. With the assistance of gravity, the fluid within the container 802 flows through both conduits 1150 and 1152 and into the port block 922. Because of the water flowing through the venturi valve 858, fluid flows from the port block 922, through the hose 940, through the valve 864 and Y fitting 862, then into the venturi valve 858 where is exits the drainage device 800 to the drain pipe 840 with the water. Because of water flowing through the first plumbing subassembly 814, fluid also travels from the port block 922, through the hose 942, through the valve 846, through the manifold 844, then into the connector 838 to then travel to the drain pipe 840.

After the fluid in the container 802 has been drained, the user rotates the swingarm 1116 back to its starting position by first pivoting the handle 1140 away from the casting 952 so as to release the engager from the ratchet teeth 1112. With the engager disengaged, the swingarm 1116 is free to rotate back to its starting position which also turns the ball valve 886 to its off position. The conduits 1150 and 1152 are then disengaged from communication with the respective inlet ports 934 and 936 and the container 802 can be removed from the drainage device 800 and properly disposed.

The drainage device 800 can also be backflushed to remove any debris in the venturi valve 858. Turning to FIG. 23, with the container 802 side activated by rotation of the swingarm 1116 or handle 1138, the backflush handle 836 is rotated which in turn rotates the output shaft 832 of the ball valve 830 of the first plumbing subassembly 814. Such rotation of the output shaft 832 closes the ball valve 830. The water that flows from the water source 896, through the hose 890, through the open ball valve 886, through the hose 884, into the venturi valve 858 then into the manifold 816 cannot exit the drainage device 800 through the first plumbing subassembly 814 because of the closed ball valve 830. Instead, water flows into the venturi valve 852, through the Y fitting 874, through the hose 876, through the valve 870, through the manifold 844, then into the connector 838 to exit the drainage device 800 to the drain pipe 840.

When backflushing is completed, the backflush handle 836 is returned to its normal position thus reopening the ball valve 830 of the first plumbing subassembly 814.

Figure 39:
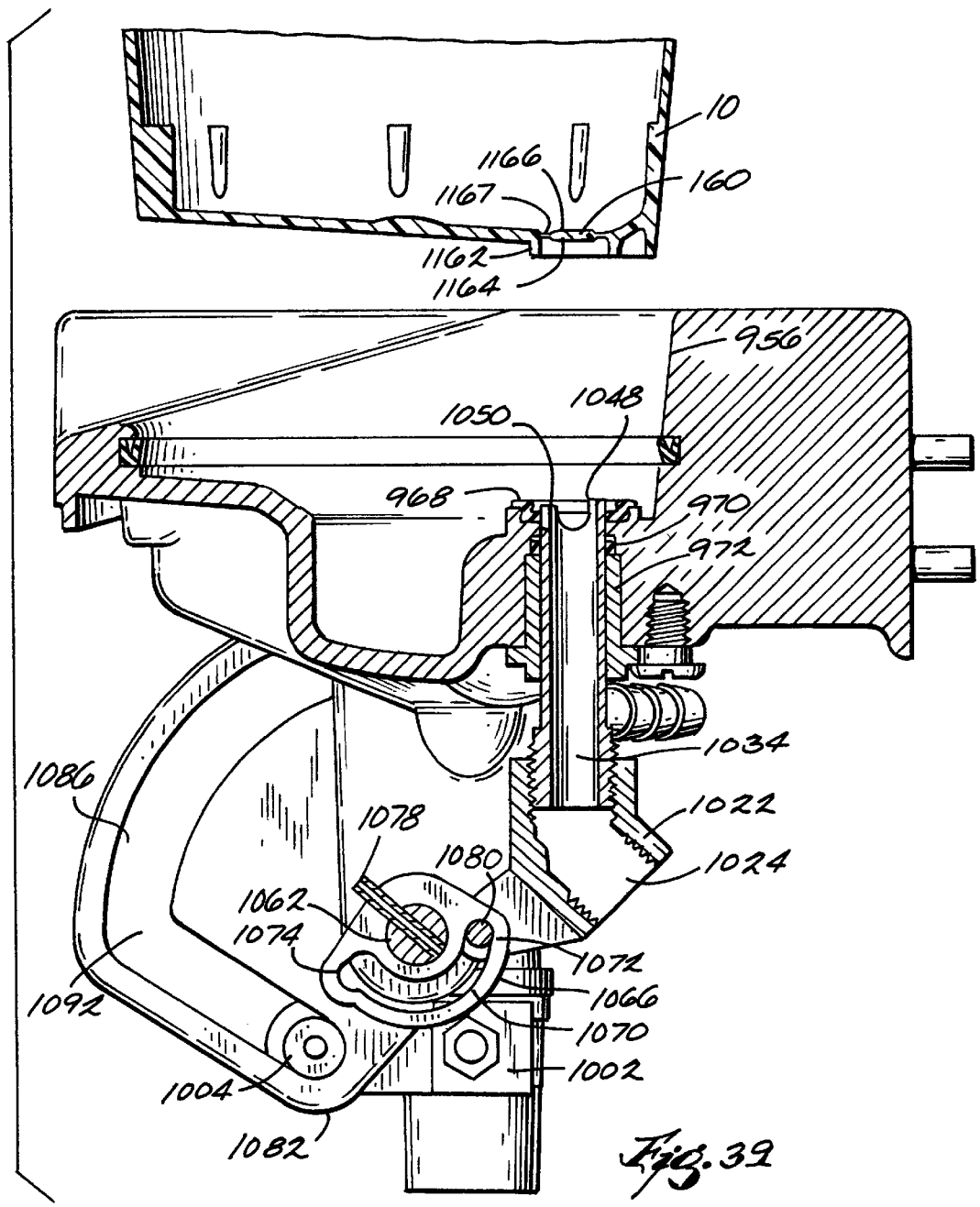
FIG. 39 is a side sectional view of the canister casting assembly in an off position.
Figure 40:
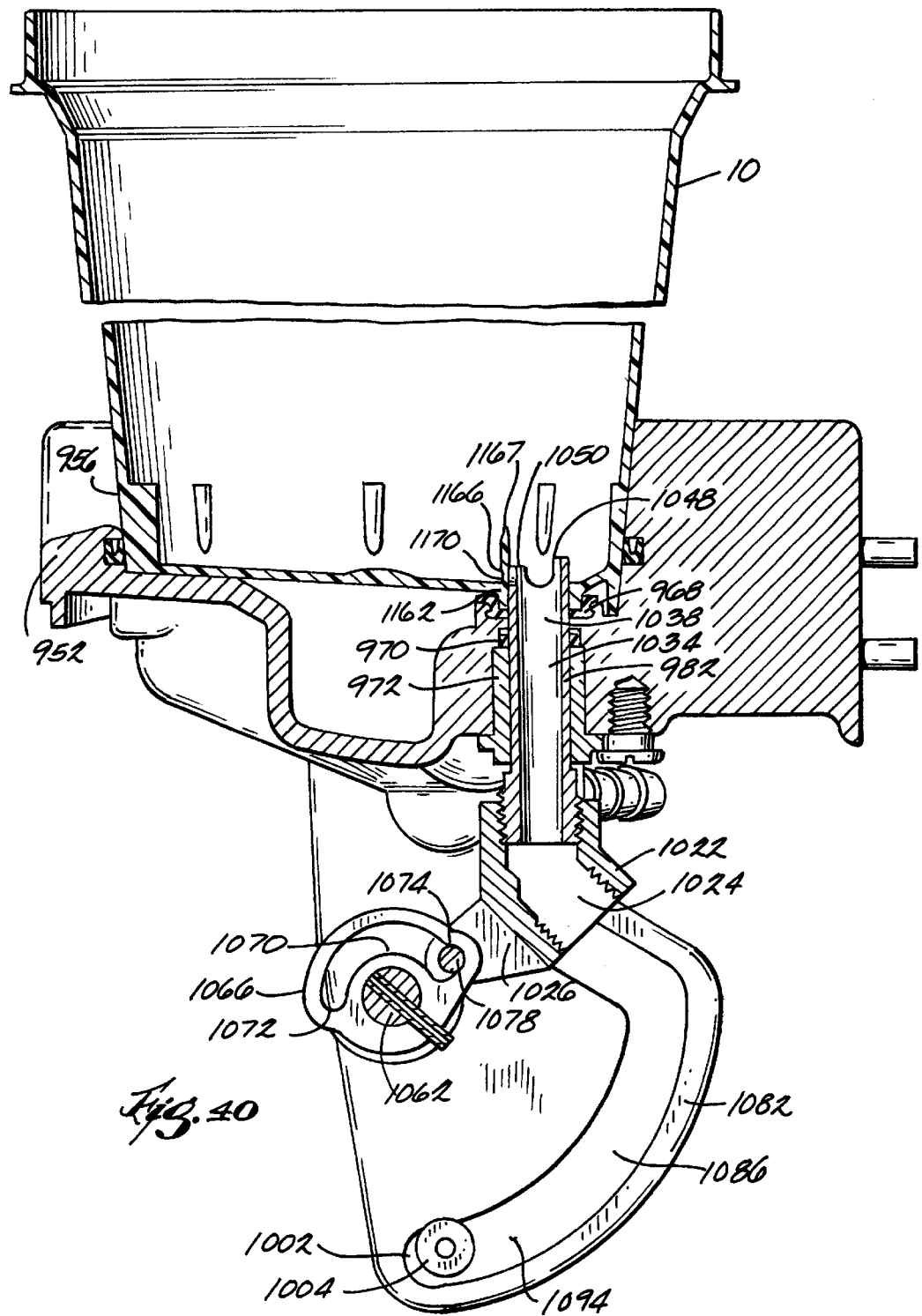
FIG. 40 is a side sectional view of the canister casting assembly in an on position.

Turning now to FIGS. 39 and 40, the drainage device 800 is operated to drain a suction canister 10 as follows. When a user desires to drain a suction canister 10, the user places the canister 10 in the recess 956 of the casting 952 such that the keyway on the canister 10 aligns with the key 964 of the casting 952. In this starting position, the cam 1066 and the cam 1082 are in the positions as shown in FIG. 39.

The user then pivots the handle 1064 (FIG. 38) a quarter turn, approximately 90 degrees, towards themselves to a first position. Rotation of the handles 1064 initiates water flow through the canister valve subassembly 990 which in turn provides a suction force through the suction port 966 to hold the canister 10 in place in the recess 956. This suction prevents a user from accidentally removing the canister 10 from the recess 956 when fluid is draining from the canister 10. Specifically, as the handle 1064 is rotated a quarter turn, the cam shaft 1062 also rotates a quarter turn along with the pipe cam 1066 and the second cam 1082 to a first position. At the end of the quarter turn, the pin 1078 connected to the pipe block 1022 has traveled from the end 1072 of the slot 1070 to the enlarged end 1074. The pin 1078 travels along a lost motion path in the slot 1070 and therefore the position of the pipe block 1022 relative to the suction canister 10 does not change. In other words, the drain pipe 1034 does not move upwardly.

As the second cam 1082 travels its 90 degrees, the cam follower 1004 is forced to move in the first portion 1092 of the slot 1086 and in an arcuate path that is counter clockwise in FIGS. 39 and 40. As the cam follower moves 1004 moves in the slot 1086, so does the valve handle 1002 thus turning on the ball valve 994 of the canister valve subassembly 990.

With the ball valve 994 turned on, and reference to FIGS. 23 and 27, water can flow from the water source 896, through the hose 894, through the valve 994, through the hose 854, through the venturi valve 852, through the manifold 816, then to the drain pipe 840 through the first plumbing subassembly 814. With the water flowing as such, suction is created at the suction port 966 because the suction port 966 is in communication with the seventh plumbing subassembly 972 via the hose 976.

As the handle 1064 is rotated through the 90 degrees, the user can hear the water flow and the suction created at the suction port 966. The user then continues to rotate the handle 1064 another 90 degrees towards themselves to a second position, for a total of 180 degrees of rotation, such that the canister cam assembly 1060 moves to its second positions as shown in FIG. 40. Specifically, as the handle 1064 is rotated, so is the cam shaft 1062 and the second cam 1082. The valve handle 1002 remains in its generally vertical position because the cam follower 1004 travels along the lost motion path in the second portion 1094 of the slot 1086 of the second cam 1082. Therefore, the ball valve 994 remains in its on position during the second 90 degree rotation of the handle 1064.

As for the pipe cam 1066, rotation of the cam shaft 1062 another 90 degrees, forces the pipe block 1022 upwardly to the ending position as shown in FIG. 40. The pipe block 1022 is forced upwardly due to the pin 1078 positioned in the enlarged end 1074 of the slot 1070. The upward movement of the pipe block 1022 moves the drain pipe 1034 upwardly to contact the suction canister 10.

Specifically, the drain pipe 1034 interacts with the suction canister 10 as follows. Referring to FIG. 39, the suction canister 10 is oriented in the recess 956 such that a drain 1160 is positioned adjacent the drain pipe 1034. The drain 1160 includes a cylindrical wall 1162 that defines a drain port 1164 that is preferably generally circular, however, other configurations of the port could also be used. A cap or cover 1166 is over the drain port 1164. Preferably, the cap 1166 is formed such that the material is thinner around the periphery 1167 of the cap 1166 than the remainder of the cap 1166 or the wall 1162.

Preferably, the wall 1162 and the cap 1166 are integral with the suction canister 10 so as to define a molded-in drain. However, it should be noted that the invention is not limited to the use of a molded-in drain. Further, preferably the drain port 1164 is located at a bottom portion 1168 of the suction canister 10, however, other locations of the drain port 1164 could also be used.

In a first or ready position shown in FIG. 39, the drain pipe 1034 is spaced from the cap 1166 and the cap 1166 covers or blocks the drain port 1164 to prevent fluid from exiting the suction canister 10 via the drain port 1164.

As the drain pipe 1034 moves upwardly, the first portion 1048 of the drain pipe 1034 to contact the cap 1166. Further upward movement of the drain pipe 1034 begins to break or sever the connection between the wall 1162 and the cap 1166 at a location adjacent the first portion 1048. Continued upward movement of the pipe drain 1034 continues to break the connection between the wall 1162 and the cap 1166 around almost, but not all of, the periphery of the cap 1166.

Because the second and third portions, 1050 and 1052 respectively, of the drain pipe 1034 terminate in the plane 1056 that is spaced from the plane 1054 in which the first portion 1048 terminates, the connection between the cap 1166 and the wall 1162 around the periphery of the cap 1166 is not completely severed. Instead, and with reference to FIG. 40, a hinge 1170 remains intact so that the cap 1166 does not completely release from the suction canister 10. As the drain pipe 1034 ceases its upward movement, the second and third portions, 1050 and 1052 respectively, cause the cap 1166 to pivot about the hinge 1170 to a generally vertical position, termed the second or draining position. The drain pipe 1034 holds or fixes the cap 1166 in this second position and does not allow the cap 1166 to move within the interior of the suction canister 10.

An advantage of a cap 1166 not completely severing from the suction canister 10 is that the cap 1166 can be positioned and maintained in that position so as not to block the drainage of the fluid through the drain pipe 1034. If the cap 1166 completely severed from the suction canister 10, the combination of the fluid flow and suction can lodge the cap 1166 over the drain pipe 1034 and block or partially block fluid flow through the passageway 1038. However, it should be noted that if desired, the drain pipe 1034 could completely sever the cap 1166 from the suction canister 10.

It should also be noted that, if desired and depending upon the plastic used to fabricate the suction canister 10, the portion of the connection between the wall 1162 and the cap 1166 that will act as the hinge 1170 can be injection molded with more plastic such that the hinge 1170 is thicker than the rest of the periphery of the connection between the wall 1162 and the cap 1166. A thicker plastic in the hinge 1170 can reinforce the hinge 1170 and further prevent the cap 1166 from completely dislodging from the suction canister 10.

Accordingly, with the cap 1166 partially severed and pivoted to its vertical position, fluid can flow from the suction canister 10, through the passageway 1038 of the pipe drain 1034, through the passageway 1024 of the pipe block 1022, through the hose 1032, through the Y fitting 880, through the valve 878, through the Y fitting 874, through the venturi valve 852, then through the manifold 816, the ball valve 830, the connector 838 to the drain pipe 840. Fluid drains from the suction canister 10 because the water flowing through the venturi valve 852, creates a suction force in the seventh plumbing subassembly 872 to draw fluid from the suction canister 10.

If desired, the user can remove any lid on the suction canister 10 and use the sprayer 1016 to clean the interior of the suction canister 10.

The gasket 968 prevents the fluid from flowing into the recess 956 of the casting 952. However, should any fluid flow into the bottom of the recess 956, the seal 962 prevents the fluid from overflowing the recess 956. Further, the suction port 966 can be used as a secondary drainage port since there is a suction force present at this port 966 and the fluid would flow into the seventh plumbing subassembly 872 and then to the drain pipe 840.

After the fluid has drained from the suction canister 10, the handle 1064 is rotated 180 degrees back to its starting position. This rotation lowers the drain pipe 1034 into the drain passageway 982 and shuts off the ball valve 994. The canister 10 can then be removed from the recess 956 and properly disposed.

The drainage device 800 can also be backflushed to remove any debris in the venturi valve 852. To perform this backflushing, and with reference to FIG. 23, the handle 836 (FIG. 37) is rotated 90 degrees such that water flows through the canister valve subassembly 990 as described above and the handle 836 is rotated 90 degrees such that the output shaft 832 of the ball valve 830 of the first plumbing subassembly 814 is rotated to close the valve 830.

Water that returns from the canister valve subassembly 990 via the hose 854, enters the venturi valve 852 and the manifold 816 but cannot exit through the valve 830 to the drain pipe 840. Instead, the water flows back into the venturi valve 858, through the Y fitting 862, through the hose 866, through the valve 848, through the manifold 844, then into the connector 838 to thus exit the drainage device 800 to the drain pipe 840.

When backflushing is completed, the backflush handle 836 is returned to its normal position thus reopening the ball valve 830 of the first plumbing subassembly 814.

While several drain arrangements and drain opening devices have been disclosed, it should be understood that other types of drains and other devices for opening drains are within the scope of the invention.

Various features of the invention are set forth in the following claims, wherein the term "container" includes suction canisters, urine collectors, chest drainage devices and other types of containers for collecting body fluids.

We claim:

1. A medical apparatus for draining bodily fluid held in a container, said apparatus comprising:
    a support area that is adapted to removably supporting the container;
    a vacuum generator in communication with said support area, said generator selectively generating a vacuum in said support area such that the vacuum holds the container in said support area;
    a tool that is actuable to alter the container such that the fluid held in the container drains from the container; and
    a cam assembly, wherein said cam assembly has a first position wherein said vacuum generator is inactive, and a second position wherein said vacuum generator creates the vacuum.

2. The medical apparatus of claim 1 wherein said cam assembly is movable into said first and second positions through movement of a handle.

3. The medical apparatus of claim 1 and further including an actuation handle operatively connected to said vacuum generator and said tool, said handle having a first position that actuates said vacuum generator and a second position that actuates said tool.

4. The medical apparatus of claim 1 wherein said tool is actuable in that said tool is movable upwardly from resting position to a position in which it is adapted to alter the container.

5. A medical apparatus for draining bodily fluid held in a container, said apparatus comprising:
    a support area that is adapted to removably supporting the container;
    a vacuum generator in communication with said support area, said generator selectively generating a vacuum in said support area such that the vacuum holds the container in said support area;
    a tool that is actuable to alter the container such that the fluid held in the container drains from the container; and
    a cam assembly operatively connected to said vacuum generator, and wherein said vacuum generator selectively generates the vacuum when said cam assembly is in a first position.

6. The medical apparatus of claim 5 wherein said tool is actuable when said cam assembly is in a second position.

7. The medical apparatus of claim 6 wherein said cam assembly must pass through said first position before entering said second position.

8. A drainage apparatus for draining bodily fluid held in a container, said apparatus comprising:
    a support area that is adapted to removably support a container;
    a vacuum generator in communication with said support area;
    an opener adapted to open the drain of a container; and
    a cam assembly operatively connected to said generator for selectively actuating said generator to create a vacuum in said support area and operatively connected to said opener for moving said opener a distance that would allow the opener to engage the container in said support area to open the drain allowing bodily fluid to flow out of the container.

9. The apparatus of claim 8 wherein said cam assembly includes a cam shaft, a first cam mounted on said shaft and connected to said generator and a second cam mounted on said shaft and connected to said opener.

10. The apparatus of claim 9 wherein rotation of said shaft a predetermined amount creates the vacuum in said support area and continued rotation of said shaft a further predetermined amount moves said opener.

11. The apparatus of claim 10 and further including a manual handle connected to said shaft.

12. The apparatus of claim 8 wherein said generator includes a venturi valve.

13. The apparatus of claim 8 wherein said opener includes a passageway and wherein when said opener is moved into engagement with the container, fluid is able to drain from the container through said passageway.

14. An apparatus for draining bodily fluids from two differing types of containers holding bodily fluid, said apparatus comprising:

a first support area for removably supporting a first type of container;

a second support area for removably supporting a second type of container;

a first inlet adapted for communication with the first type of container, said first inlet accepting bodily fluid drained from the first type of container;

a second inlet adapted for communication with the second type of container, said second inlet accepting bodily fluid drained from the second type of container; and a vacuum generator for creating a vacuum at said first inlet and said second inlet.

15. The apparatus of claim 14 wherein said generator includes a first venturi valve for creating a vacuum at said first inlet and a second venturi valve for creating a vacuum at said second inlet.

16. The apparatus of claim 15 wherein said generator includes a Y-type manifold in communication with said first and second venturi valves.

17. The apparatus of claim 14 wherein said generator creates a vacuum at one of said first or second support areas to hold the respective container in said one of said first and second support areas.

18. The apparatus of claim 14 and further including an actuation handle in communication with said vacuum generator.

19. The apparatus of claim 14 and further including means for backflushing at least one of said first and second venturi valves.

20. The apparatus of claim 14 and further including a sprayer in communication with a source of cleaning fluid.

21. A method for draining bodily fluid from a container, said method comprising the steps:

positioning a container having bodily fluids therein on a support area of a drainage device;

moving a cam assembly in the drainage device to a first position wherein a vacuum is created in the support area to hold the container in place; and moving the cam assembly to a second position wherein a tool of the drainage device alters the container to release the bodily fluid from the container.

22. A method for draining bodily fluids from a container, said method comprising the steps:

positioning a container having bodily fluids therein on a support area of a drainage device;

creating a vacuum in the support area to hold the container in place; and operating the drainage device with a rotatable handle to alter the container to drain the bodily fluid from the container.

23. The method of claim 22 wherein in the creating step, the vacuum is created by a fluid moving through a venturi.

24. The method of claim 23 wherein the fluid includes water.

25. The method of claim 22 wherein in the operating step, a tool is moved upwardly to alter the container.

26. The method of claim 22 wherein in the operating step, the container is permanently altered by the drainage device opening a drain port in the container.

27. The method of claim 26 wherein the drain port is in a bottom surface of the container.

28. The method of claim 22 wherein in the positioning step, the support area is a recess.

29. The method of claim 22 wherein rotation of the handle actuates the creation of the vacuum.

30. The method of claim 22 wherein the container is a suction canister.

* * * * *